US 7,253,270 B2

(12) United States Patent
Serres

(10) Patent No.: US 7,253,270 B2
(45) Date of Patent: Aug. 7, 2007

(54) POLYNUCLEOTIDE ENCODING A MUTATED HIV GP41 POLYPEPTIDE

(75) Inventor: Pierre F Serres, Saint Genis Laval (FR)

(73) Assignee: Mymetics SA, Saint Genis Laval (FR)

( * ) Notice: Subject to any disclaimer, the term of this patent is extended or adjusted under 35 U.S.C. 154(b) by 0 days.

(21) Appl. No.: 10/198,938

(22) Filed: Jul. 22, 2002

(65) Prior Publication Data

US 2004/0014046 A1  Jan. 22, 2004
US 2005/0048478 A9  Mar. 3, 2005

Related U.S. Application Data

(60) Division of application No. 09/570,921, filed on May 15, 2000, which is a continuation of application No. PCT/FR98/02447, filed on Nov. 17, 1998, now Pat. No. 6,455,265.

(30) Foreign Application Priority Data

Nov. 17, 1997 (FR) .................................. 97 14387

(51) Int. Cl.
C07H 21/00 (2006.01)
A61K 39/21 (2006.01)
(52) U.S. Cl. .................................. 536/23.1; 424/208.1
(58) Field of Classification Search ................. 435/7.1, 435/5, 69.1; 530/300; 536/23.1
See application file for complete search history.

(56) References Cited

U.S. PATENT DOCUMENTS 6,455,265 B1 *  9/2002  Serres ........................ 435/7.1
6,824,783 B1 * 11/2004  Bolognesi et al. ....... 424/188.1

FOREIGN PATENT DOCUMENTS

WO    WO 93 01304    1/1993
WO    WO 94 02505    2/1994
WO    WO 94 06471    3/1994

OTHER PUBLICATIONS

Steuler et al. Distinct Populations of Human Immunodeficiency Virus Type 1 in Blood and Cerebrospinal Fluid, AIDS Research and Human Retroviruses, 1992, 8(1):53-59.*
R. P. Johnson et al., "Identification of overlapping HLA class I-restricted cytotoxic T cell epitopes in a conserved region of the human immunodeficiency virus type I envelope glycoprotein: definition of minimum epitopes and analysis of the effects of sequence variation," *Journal of Experimental Medicine*, Apr. 1, 1992, 175(4) pp. 961-971.
Fahey et al., "Status of immune-based therapies in HIV infection and AIDS," *Clin. Exp. Immunol.*, vol. 88, pp. 1-5, 1992.
Fox, J. "No winners against AIDS," *Bio/Technology*, vol. 12, p. 128, 1994.
Haynes et al., "Update on the Issues of HIV Vaccine Development," *The Finnish Medical Society DUODECIM, Ann Med*, vol. 28, pp. 39-41, 1996.
Reiher, Walter E., III, et al., "Sequence homology between acquired immunodeficiency syndrome virus envelope protein and interleukin 2," Proc. Natl. Acad. Sci. USA, vol. 83, pp. 9188-9192, Dec. 1986.
Bost, K. L., et al., "Individuals infected with HIV possess antibodies against IL-2," Immunology, vol. 65, pp. 611-615, 1988.
Levy, Jay A., "Pathogenesis of Human Immunodeficiency Virus Infection," Microbiological Reviews, vol. 57, No. 1, pp. 183-289, Mar. 1993.

* cited by examiner

*Primary Examiner*—Stacy B. Chen
(74) *Attorney, Agent, or Firm*—Oliff & Berridge PLC

(57) ABSTRACT

The invention provides a method of searching for and obtaining a vaccine against the pathogenic effects related to the infection of an animal or human host by a retrovirus that penetrates into a target cell of the host, and a vaccine obtained by the method are provided. The method includes preparing candidate vaccine agents based on a polypeptide comprising at least part of an envelope protein of a pathogenic strain of the retrovirus and selecting as the vaccine a modified polypeptide chosen from polypeptides that induces an immune response directed against an immunodominant region of an envelope protein of the retrovirus and not against a protein of the host.

1 Claim, No Drawings

SEQUENCE LISTING

```
<160> NUMBER OF SEQ ID NOS: 144

<210> SEQ ID NO 1
<211> LENGTH: 138
<212> TYPE: PRT
<213> ORGANISM: Human

<400> SEQUENCE: 1

Gln Ala Arg Gln Leu Leu Ser Gly Ile Val Gln Gln Gln Asn Asn Leu
 1               5                  10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Leu Ile
    50                  55                  60

Cys Thr Thr Thr Val Pro Trp Asn Ser Ser Trp Ser Asn Arg Ser Leu
65                  70                  75                  80

Asn Asp Ile Trp Gln Asn Met Thr Trp Met Glu Trp Glu Arg Glu Ile
                85                  90                  95

Asp Asn Tyr Thr Gly Leu Ile Tyr Arg Leu Ile Glu Glu Ser Gln Thr
            100                 105                 110

Gln Gln Glu Lys Asn Glu Gln Glu Leu Leu Glu Leu Asp Lys Trp Ala
        115                 120                 125

Ser Leu Trp Asn Trp Phe Asn Ile Thr Gln
    130                 135

<210> SEQ ID NO 2
<211> LENGTH: 138
<212> TYPE: PRT
<213> ORGANISM: Human

<400> SEQUENCE: 2

Gln Ala Arg Gln Leu Met Ser Gly Ile Val Gln Gln Gln Asn Asn Leu
 1               5                  10                  15
```

```
Leu Arg Ala Ile Glu Ala Gln Gln His Leu Gln Leu Thr Val Trp
            20                  25                  30

Gly Ile Lys Gln Leu Gln Ala Arg Ile Leu Ala Val Glu Arg Tyr Leu
            35                  40                  45

Lys Asp Gln Gln Leu Leu Gly Ile Trp Gly Cys Ser Gly Lys Leu Ile
            50                  55                  60

Cys Thr Thr Thr Val Pro Trp Asn Ser Ser Trp Ser Asn Arg Ser Leu
 65                  70                  75                  80

Asn Asp Ile Trp Gln Asn Met Thr Trp Met Glu Trp Glu Arg Glu Ile
                    85                  90                  95

Asp Asn Tyr Thr Gly Leu Ile Tyr Arg Leu Ile Glu Glu Ser Gln Thr
                100                 105                 110

Gln Gln Glu Lys Asn Glu Gln Glu Leu Leu Glu Leu Asp Lys Trp Ala
            115                 120                 125

Ser Leu Trp Asn Trp Phe Asn Ile Thr Gln
        130                 135
```

<210> SEQ ID NO 3
<211> LENGTH: 138
<212> TYPE: PRT
<213> ORGANISM: Human

<400> SEQUENCE: 3

```
Gln Ala Arg Gln Leu Met Ser Gly Ile Val Gln Gln Asn Asn Leu
 1               5                  10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
            35                  40                  45

Lys Asp Gln Gln Leu Leu Gly Ile Trp Gly Cys Ser Gly Lys His Ile
            50                  55                  60

Cys Thr Thr Asn Val Pro Trp Asn Ser Ser Trp Ser Asn Arg Ser Leu
 65                  70                  75                  80

Asn Glu Ile Trp Gln Asn Met Thr Trp Met Glu Trp Glu Arg Glu Ile
                    85                  90                  95

Asp Asn Tyr Thr Gly Leu Ile Tyr Ser Leu Ile Glu Glu Ser Gln Thr
                100                 105                 110

Gln Gln Glu Lys Asn Glu Lys Glu Leu Leu Glu Leu Asp Lys Trp Ala
            115                 120                 125

Ser Leu Trp Asn Trp Phe Ser Ile Thr Gln
        130                 135
```

<210> SEQ ID NO 4
<211> LENGTH: 138
<212> TYPE: PRT
<213> ORGANISM: Human

<400> SEQUENCE: 4

```
Gln Ala Arg Gln Leu Met Ser Gly Ile Val His Gln Gln Asn Asn Leu
 1               5                  10                  15

Leu Arg Ala Ile Glu Ala Gln Gln His Leu Leu Gln Leu Thr Val Trp
            20                  25                  30

Gly Ile Lys Gln Leu Gln Ala Arg Val Leu Ala Val Glu Arg Tyr Leu
            35                  40                  45

Arg Asp Gln Gln Leu Leu Gly Ile Trp Gly Cys Ser Gly Arg His Ile
            50                  55                  60
```

```
Cys Thr Thr Asn Val Pro Trp Asn Ser Ser Trp Ser Asn Arg Ser Leu
 65                  70                  75                  80

Asp Glu Ile Trp Gln Asn Met Thr Trp Met Glu Trp Glu Arg Glu Ile
                 85                  90                  95

Asp Asn Tyr Thr Gly Leu Ile Tyr Ser Leu Ile Glu Gly Ser Gln Ile
            100                 105                 110

Gln Gln Glu Lys Asn Glu Lys Glu Leu Leu Glu Leu Asp Lys Trp Ala
        115                 120                 125

Ser Leu Trp Asn Trp Phe Ser Ile Thr Lys
    130                 135

<210> SEQ ID NO 5
<211> LENGTH: 138
<212> TYPE: PRT
<213> ORGANISM: Human

<400> SEQUENCE: 5

Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
             20                  25                  30

Gly Ile Lys Gln Leu Gln Ala Arg Val Leu Ala Val Glu Arg Tyr Leu
         35                  40                  45

Gln Asp Gln Arg Leu Leu Gly Met Trp Gly Cys Ser Gly Lys His Ile
     50                  55                  60

Cys Thr Thr Phe Val Pro Trp Asn Ser Ser Trp Ser Asn Arg Ser Leu
 65                  70                  75                  80

Asp Asp Ile Trp Asn Asn Met Thr Trp Met Gln Trp Glu Lys Glu Ile
                 85                  90                  95

Ser Asn Tyr Thr Gly Ile Ile Tyr Asn Leu Ile Glu Glu Ser Gln Ile
            100                 105                 110

Gln Gln Glu Lys Asn Glu Lys Glu Leu Leu Glu Leu Asp Lys Trp Ala
        115                 120                 125

Ser Leu Trp Asn Trp Phe Ser Ile Ser Lys
    130                 135

<210> SEQ ID NO 6
<211> LENGTH: 138
<212> TYPE: PRT
<213> ORGANISM: Human

<400> SEQUENCE: 6

Gln Ala Arg Gln Leu Leu Ser Gly Ile Val Gln Gln Gln Asn Asn Leu
  1               5                  10                  15

Leu Arg Ala Ile Glu Ala Gln Gln His Met Leu Gln Leu Thr Val Trp
             20                  25                  30

Gly Ile Lys Gln Leu Gln Ala Arg Val Leu Ala Val Glu Ser Tyr Leu
         35                  40                  45

Lys Asp Gln Gln Leu Leu Gly Ile Trp Gly Cys Ser Gly Lys His Ile
     50                  55                  60

Cys Thr Thr Thr Val Pro Trp Asn Ser Ser Trp Ser Asn Lys Ser Leu
 65                  70                  75                  80

Glu Glu Ile Trp Asn Asn Met Thr Trp Ile Glu Trp Glu Arg Glu Ile
                 85                  90                  95

Asp Asn Tyr Thr Gly Val Ile Tyr Ser Leu Ile Glu Asn Ser Gln Ile
            100                 105                 110
```

```
Gln Gln Glu Lys Asn Glu Gln Asp Leu Leu Gln Leu Asp Lys Trp Ala
            115                 120                 125

Ser Leu Trp Asn Trp Phe Ser Ile Thr Lys
130                 135

<210> SEQ ID NO 7
<211> LENGTH: 138
<212> TYPE: PRT
<213> ORGANISM: Human

<400> SEQUENCE: 7

Gln Ala Arg Gln Leu Leu Ser Gly Ile Val Gln Gln Gln Asn Asn Leu
1               5                   10                  15

Leu Arg Ala Ile Lys Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Leu Leu Gly Phe Trp Gly Cys Ser Gly Lys Leu Ile
    50                  55                  60

Cys Thr Thr Ala Val Pro Trp Asn Ala Ser Trp Ser Asn Lys Thr Leu
65                  70                  75                  80

Asp Gln Ile Trp Asn Asn Met Thr Trp Met Glu Trp Asp Arg Glu Ile
                85                  90                  95

Asp Asn Tyr Thr His Leu Ile Tyr Thr Leu Ile Glu Glu Ser Gln Asn
            100                 105                 110

Gln Gln Glu Lys Asn Gln Glu Leu Leu Gln Leu Asp Lys Trp Ala
            115                 120                 125

Ser Leu Trp Thr Trp Ser Asp Ile Thr Lys
130                 135

<210> SEQ ID NO 8
<211> LENGTH: 138
<212> TYPE: PRT
<213> ORGANISM: Human

<400> SEQUENCE: 8

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Val Leu Ala Val Glu Arg Tyr Leu
        35                  40                  45

Lys Asp Gln Gln Leu Leu Gly Ile Trp Gly Cys Ser Gly Lys Leu Ile
    50                  55                  60

Cys Thr Thr Ala Val Pro Trp Asn Ala Ser Trp Ser Asn Lys Ser Leu
65                  70                  75                  80

Asp Gln Ile Trp Asn Asn Met Thr Trp Met Glu Trp Glu Arg Glu Ile
                85                  90                  95

Asp Asn Tyr Thr Asn Leu Ile Tyr Thr Leu Ile Glu Glu Ser Gln Asn
            100                 105                 110

Gln Gln Glu Lys Asn Glu Gln Glu Leu Leu Glu Leu Asp Lys Trp Ala
            115                 120                 125

Ser Leu Trp Asn Trp Phe Asp Ile Ser Lys
130                 135

<210> SEQ ID NO 9
<211> LENGTH: 138
```

```
<212> TYPE: PRT
<213> ORGANISM: Human

<400> SEQUENCE: 9

Gln Ala Arg Leu Leu Leu Ser Gly Ile Val Gln Gln Gln Asn Asn Leu
  1               5                  10                  15

Leu Met Ala Ile Glu Ala Gln Gln His Met Leu Glu Leu Thr Val Trp
             20                  25                  30

Gly Ile Lys Gln Leu Gln Ala Arg Val Leu Ala Val Glu Arg Tyr Leu
         35                  40                  45

Lys Asp Gln Gln Leu Leu Gly Ile Trp Gly Cys Ser Gly Lys Leu Ile
     50                  55                  60

Cys Thr Thr Ala Val Pro Trp Asn Ala Ser Trp Ser Asn Lys Ser Leu
 65                  70                  75                  80

Ser Asp Ile Trp Asp Asn Met Thr Trp Met Glu Trp Glu Arg Glu Ile
                 85                  90                  95

Asp Asn Tyr Thr Asn Leu Ile Tyr Ser Leu Ile Glu Asp Ser Gln Ile
            100                 105                 110

Gln Gln Glu Lys Asn Glu Lys Glu Leu Leu Glu Leu Asp Lys Trp Ala
        115                 120                 125

Ser Leu Trp Asn Trp Phe Asn Ile Thr Asn
    130                 135

<210> SEQ ID NO 10
<211> LENGTH: 138
<212> TYPE: PRT
<213> ORGANISM: Human

<400> SEQUENCE: 10

Gln Ala Arg Gln Leu Leu Ser Gly Ile Val Gln Gln Gln Asn Asn Leu
  1               5                  10                  15

Leu Arg Ala Ile Glu Ala Gln Gln His Met Leu Gln Leu Thr Val Trp
             20                  25                  30

Gly Ile Lys Gln Leu Gln Ala Arg Val Leu Ala Val Glu Arg Tyr Leu
         35                  40                  45

Lys Asp Gln Gln Leu Met Gly Ile Trp Gly Cys Ser Gly Lys Leu Ile
     50                  55                  60

Cys Thr Thr Ala Val Pro Trp Asn Thr Ser Trp Ser Asn Lys Ser Leu
 65                  70                  75                  80

Asp Ser Ile Trp Asn Asn Met Thr Trp Met Glu Trp Glu Lys Glu Ile
                 85                  90                  95

Glu Asn Tyr Thr Asn Thr Ile Tyr Thr Leu Ile Glu Glu Ser Gln Ile
            100                 105                 110

Gln Gln Glu Lys Asn Glu Gln Glu Leu Leu Glu Leu Asp Lys Trp Ala
        115                 120                 125

Ser Leu Trp Asn Trp Phe Gly Ile Thr Lys
    130                 135

<210> SEQ ID NO 11
<211> LENGTH: 138
<212> TYPE: PRT
<213> ORGANISM: Human

<400> SEQUENCE: 11

Gln Ala Arg Leu Leu Leu Ser Gly Ile Val Gln Gln Gln Asn Asn Leu
  1               5                  10                  15

Leu Arg Ala Ile Glu Gly Gln Gln His Leu Leu Gln Leu Thr Val Trp
             20                  25                  30
```

```
                     20                  25                  30
Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Leu Ile
    50                  55                  60

Cys Thr Thr Ala Val Pro Trp Asn Ala Ser Trp Ser Asn Lys Ser Leu
65                  70                  75                  80

Glu Glu Ile Trp Asp Asn Met Thr Trp Met Glu Trp Glu Arg Glu Ile
                85                  90                  95

Asp Asn Tyr Thr Ser Leu Ile Tyr Thr Leu Ile Glu Glu Ser Gln Asn
            100                 105                 110

Gln Gln Glu Lys Asn Glu Gln Glu Leu Leu Gly Leu Asp Lys Trp Ala
        115                 120                 125

Ser Leu Trp Asn Trp Phe Thr Ile Thr Asn
    130                 135

<210> SEQ ID NO 12
<211> LENGTH: 138
<212> TYPE: PRT
<213> ORGANISM: Human

<400> SEQUENCE: 12

Gln Ala Arg Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Val Leu Ala Val Glu Arg Tyr Leu
        35                  40                  45

Arg Asp Gln Gln Leu Leu Gly Ile Trp Gly Cys Ser Gly Lys Leu Ile
    50                  55                  60

Cys Thr Thr Thr Val Pro Trp Asn Thr Ser Trp Ser Asn Lys Ser Leu
65                  70                  75                  80

Asp Lys Ile Trp Gly Asn Met Thr Trp Met Glu Trp Glu Arg Glu Ile
                85                  90                  95

Asp Asn Tyr Thr Ser Leu Ile Tyr Thr Leu Ile Glu Glu Ser Gln Asn
            100                 105                 110

Gln Gln Glu Lys Asn Glu Gln Glu Leu Leu Glu Leu Asp Lys Trp Ala
        115                 120                 125

Ser Leu Trp Asn Trp Phe Asn Ile Thr Asn
    130                 135

<210> SEQ ID NO 13
<211> LENGTH: 138
<212> TYPE: PRT
<213> ORGANISM: Human

<400> SEQUENCE: 13

Gln Ala Arg Gln Leu Leu Pro Gly Ile Val Gln Gln Gln Asn Asn Leu
1               5                   10                  15

Leu Arg Ala Ile Asp Ala Gln Gln His Leu Leu Gln Leu Thr Val Trp
                20                  25                  30

Gly Ile Lys Gln Leu Gln Ala Arg Val Leu Ala Val Glu Arg Tyr Leu
        35                  40                  45

Lys Asp Gln Gln Leu Met Gly Ile Trp Gly Cys Ser Gly Lys Phe Ile
    50                  55                  60

Cys Thr Thr Ala Val Pro Trp Asn Thr Ser Trp Ser Asn Lys Ser Phe
```

```
            65                  70                  75                  80
Asn Glu Ile Trp Asp Asn Met Thr Trp Met Glu Trp Glu Arg Glu Ile
                85                  90                  95
Asn Asn Tyr Thr Asn Leu Ile Tyr Asn Leu Ile Glu Glu Ser Gln Asn
               100                 105                 110
Gln Gln Glu Lys Asn Glu Gln Asp Leu Leu Ala Leu Asp Lys Trp Asp
           115                 120                 125
Ser Leu Trp Asn Trp Phe Ser Ile Thr Lys
       130                 135
```

<210> SEQ ID NO 14
<211> LENGTH: 138
<212> TYPE: PRT
<213> ORGANISM: Human

<400> SEQUENCE: 14

```
Gln Ala Arg Gln Leu Leu Ser Gly Ile Val Gln Gln Gln Asn Asn Leu
  1               5                  10                  15
Leu Arg Ala Ile Glu Ala Gln Gln His Leu Leu Gln Leu Thr Val Trp
                20                  25                  30
Gly Ile Lys Gln Leu Gln Ala Arg Val Leu Ala Val Glu Arg Tyr Leu
            35                  40                  45
Arg Asp Gln Gln Leu Leu Gly Ile Trp Gly Cys Ser Gly Lys Leu Ile
 50                  55                  60
Cys Thr Thr Thr Val Pro Trp Asn Thr Ser Trp Ser Asn Lys Ser Leu
 65                  70                  75                  80
Asn Glu Ile Trp Asp Asn Met Thr Trp Met Lys Trp Glu Arg Glu Ile
                85                  90                  95
Asp Asn Tyr Thr His Ile Ile Tyr Ser Leu Ile Glu Gln Ser Gln Asn
               100                 105                 110
Gln Gln Glu Lys Asn Glu Gln Glu Leu Leu Ala Leu Asp Lys Trp Ala
           115                 120                 125
Ser Leu Trp Asn Trp Phe Asp Ile Thr Lys
       130                 135
```

<210> SEQ ID NO 15
<211> LENGTH: 138
<212> TYPE: PRT
<213> ORGANISM: Human

<400> SEQUENCE: 15

```
Gln Ala Arg Leu Leu Leu Ser Gly Ile Val Gln Gln Gln Asn Asn Leu
  1               5                  10                  15
Leu Arg Ala Ile Glu Ala Gln Gln His Met Leu Gln Leu Thr Val Trp
                20                  25                  30
Gly Ile Lys Gln Leu Gln Ala Arg Val Leu Ala Val Glu Arg Tyr Leu
            35                  40                  45
Lys Asp Gln Gln Leu Leu Gly Phe Trp Gly Cys Ser Gly Lys Leu Ile
 50                  55                  60
Cys Thr Thr Thr Val Pro Trp Asn Ala Ser Trp Ser Asn Lys Ser Leu
 65                  70                  75                  80
Asp Asp Ile Trp Asn Asn Met Thr Trp Met Gln Trp Glu Arg Glu Ile
                85                  90                  95
Asp Asn Tyr Thr Ser Leu Ile Tyr Ser Leu Leu Glu Lys Ser Gln Thr
               100                 105                 110
Gln Gln Glu Lys Asn Glu Gln Glu Leu Leu Glu Leu Asp Lys Trp Ala
```

```
                115                 120                 125

Ser Leu Trp Asn Trp Phe Asp Ile Thr Asn
    130                 135

<210> SEQ ID NO 16
<211> LENGTH: 138
<212> TYPE: PRT
<213> ORGANISM: Human

<400> SEQUENCE: 16

Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
                 20                  25                  30

Gly Ile Lys Gln Leu Gln Ala Arg Val Leu Ala Val Glu Arg Tyr Leu
             35                  40                  45

Arg Asp Gln Gln Leu Leu Gly Ile Trp Gly Cys Ser Gly Lys Leu Ile
 50                  55                  60

Cys Thr Thr Ala Val Pro Trp Asn Ala Ser Trp Ser Asn Lys Ser Leu
 65                  70                  75                  80

Glu Asp Ile Trp Asp Asn Met Thr Trp Met Gln Trp Glu Arg Glu Ile
                 85                  90                  95

Asp Asn Tyr Thr Asn Thr Ile Tyr Thr Leu Leu Glu Glu Ser Gln Asn
            100                 105                 110

Gln Gln Glu Lys Asn Glu Gln Glu Leu Leu Glu Leu Asp Lys Trp Ala
            115                 120                 125

Ser Leu Trp Asn Trp Phe Ser Ile Thr Asn
    130                 135

<210> SEQ ID NO 17
<211> LENGTH: 138
<212> TYPE: PRT
<213> ORGANISM: Human

<400> SEQUENCE: 17

Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
                 20                  25                  30

Gly Ile Lys Gln Leu Gln Ala Arg Val Leu Ala Val Glu Arg Tyr Leu
             35                  40                  45

Lys Asp Gln Gln Leu Leu Gly Ile Trp Gly Cys Ser Gly Lys Leu Ile
 50                  55                  60

Cys Thr Thr Thr Val Pro Trp Asn Ala Ser Trp Ser Asn Lys Ser Leu
 65                  70                  75                  80

Asn Glu Ile Trp Asp Asn Met Thr Trp Met Gln Trp Glu Arg Glu Ile
                 85                  90                  95

Asp Asn Tyr Thr His Leu Ile Tyr Thr Leu Ile Glu Glu Ser Gln Asn
            100                 105                 110

Gln Gln Glu Lys Asn Glu Gln Glu Leu Leu Glu Leu Asp Lys Trp Ala
            115                 120                 125

Gly Leu Trp Ser Trp Phe Ser Ile Thr Asn
    130                 135

<210> SEQ ID NO 18
<211> LENGTH: 138
<212> TYPE: PRT
```

<213> ORGANISM: Human

<400> SEQUENCE: 18

Gln Ala Arg His Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Val Leu Ala Val Glu Arg Tyr Leu
        35                  40                  45

Arg Asp Gln Gln Leu Leu Gly Ile Trp Gly Cys Ser Gly Lys Leu Ile
    50                  55                  60

Cys Thr Thr Thr Val Pro Trp Asn Ala Ser Trp Ser Asn Lys Ser Leu
65                  70                  75                  80

Asn Met Ile Trp Asn Met Thr Trp Met Gln Trp Glu Arg Glu Ile
                85                  90                  95

Asp Asn Tyr Thr Gly Ile Ile Tyr Asn Leu Leu Glu Glu Ser Gln Asn
            100                 105                 110

Gln Gln Glu Lys Asn Glu Gln Glu Leu Leu Glu Leu Asp Lys Trp Ala
        115                 120                 125

Asn Leu Trp Asn Trp Phe Asp Ile Thr Gln
    130                 135

<210> SEQ ID NO 19
<211> LENGTH: 138
<212> TYPE: PRT
<213> ORGANISM: Human

<400> SEQUENCE: 19

Gln Ala Arg Lys Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Val Leu Ala Val Glu Arg Tyr Leu
        35                  40                  45

Arg Asp Gln Gln Leu Leu Gly Ile Trp Gly Cys Ser Gly Lys Leu Ile
    50                  55                  60

Cys Thr Thr Thr Val Pro Trp Asn Thr Ser Trp Ser Asn Lys Ser Leu
65                  70                  75                  80

Asp Lys Ile Trp Asn Asn Met Thr Trp Met Glu Trp Glu Arg Glu Ile
                85                  90                  95

Asp Asn Tyr Thr Ser Leu Ile Tyr Thr Leu Leu Glu Glu Ser Gln Asn
            100                 105                 110

Gln Gln Glu Lys Asn Glu Gln Glu Leu Leu Glu Leu Asp Lys Trp Ala
        115                 120                 125

Ser Leu Trp Asn Trp Phe Ser Ile Thr Asn
    130                 135

<210> SEQ ID NO 20
<211> LENGTH: 138
<212> TYPE: PRT
<213> ORGANISM: Human

<400> SEQUENCE: 20

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

```
Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Leu Ile
        50                  55                  60

Cys Thr Thr Ala Val Pro Trp Asn Ala Ser Trp Ser Asn Lys Ser Leu
 65                  70                  75                  80

Glu Gln Ile Trp Asn His Thr Thr Trp Met Glu Trp Asp Arg Glu Ile
                85                  90                  95

Asn Asn Tyr Thr Ser Leu Ile His Ser Leu Ile Glu Glu Ser Gln Asn
               100                 105                 110

Gln Gln Glu Lys Asn Glu Gln Glu Leu Leu Glu Leu Asp Lys Trp Ala
           115                 120                 125

Ser Leu Trp Asn Trp Phe Asn Ile Thr Asn
        130                 135

<210> SEQ ID NO 21
<211> LENGTH: 138
<212> TYPE: PRT
<213> ORGANISM: Human

<400> SEQUENCE: 21

Gln Ala Arg Gln Leu Leu Ser Gly Ile Val Gln Gln Gln Asn Asn Leu
 1               5                  10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Leu Leu
        50                  55                  60

Cys Thr Thr Ala Val Pro Trp Asn Ala Ser Trp Ser Asn Lys Ser Leu
 65                  70                  75                  80

Glu Gln Ile Trp Asn His Thr Thr Trp Met Glu Trp Asp Arg Glu Ile
                85                  90                  95

Asn Asn Tyr Thr Ser Leu Ile His Ser Leu Ile Glu Glu Ser Gln Asn
               100                 105                 110

Gln Gln Glu Lys Asn Glu Gln Glu Leu Leu Glu Leu Asp Lys Trp Ala
           115                 120                 125

Ser Leu Trp Asn Trp Phe Asn Ile Thr Asn
        130                 135

<210> SEQ ID NO 22
<211> LENGTH: 138
<212> TYPE: PRT
<213> ORGANISM: Human

<400> SEQUENCE: 22

Gln Ala Arg Gln Leu Leu Ser Gly Ile Val Gln Gln Gln Asn Asn Leu
 1               5                  10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Leu Ile
        50                  55                  60

Cys Thr Thr Ala Val Pro Trp Asn Ala Ser Trp Ser Asn Lys Ser Leu
 65                  70                  75                  80
```

```
Glu Gln Ile Trp Asn Asn Met Thr Trp Met Glu Trp Asp Arg Glu Ile
                 85                  90                  95

Asn Asn Tyr Thr Ser Leu Ile His Ser Leu Ile Glu Glu Ser Gln Asn
            100                 105                 110

Gln Gln Glu Lys Asn Glu Gln Glu Leu Leu Glu Leu Asp Lys Trp Ala
        115                 120                 125

Ser Leu Trp Asn Trp Phe Asn Ile Thr Asn
    130                 135

<210> SEQ ID NO 23
<211> LENGTH: 138
<212> TYPE: PRT
<213> ORGANISM: Human

<400> SEQUENCE: 23

Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
             20                  25                  30

Gly Ile Lys Gln Leu Gln Ala Arg Ile Leu Ala Val Glu Arg Tyr Leu
         35                  40                  45

Lys Asp Gln Gln Leu Leu Gly Ile Trp Gly Cys Ser Gly Lys Leu Ile
     50                  55                  60

Cys Thr Thr Ala Val Pro Trp Asn Ala Ser Trp Ser Asn Lys Ser Leu
 65                  70                  75                  80

Glu Gln Ile Trp Asn Asn Met Thr Trp Met Glu Trp Asp Arg Glu Ile
                 85                  90                  95

Asn Asn Tyr Thr Ser Leu Ile His Ser Leu Ile Glu Glu Ser Gln Asn
            100                 105                 110

Gln Gln Glu Lys Asn Glu Gln Glu Leu Leu Glu Leu Asp Lys Trp Ala
        115                 120                 125

Asn Leu Trp Asn Trp Leu Asn Ile Thr Asn
    130                 135

<210> SEQ ID NO 24
<211> LENGTH: 138
<212> TYPE: PRT
<213> ORGANISM: Human

<400> SEQUENCE: 24

Gln Ala Arg Gln Leu Leu Ser Gly Ile Val Gln Gln Gln Asn Asn Leu
  1               5                  10                  15

Leu Arg Ala Ile Glu Gly Gln Gln His Leu Leu Gln Leu Thr Val Trp
             20                  25                  30

Gly Ile Lys Gln Leu Gln Ala Arg Ile Leu Ala Val Glu Arg Tyr Leu
         35                  40                  45

Lys Asp Gln Gln Leu Leu Gly Ile Trp Gly Cys Ser Gly Lys Leu Ile
     50                  55                  60

Cys Thr Thr Ala Val Pro Trp Asn Ala Ser Trp Ser Asn Lys Ser Leu
 65                  70                  75                  80

Glu Gln Ile Trp Asn Asn Met Thr Trp Met Glu Trp Asp Arg Glu Ile
                 85                  90                  95

Asn Asn Tyr Thr Ser Leu Ile His Ser Leu Ile Glu Glu Ser Gln Asn
            100                 105                 110

Gln Gln Glu Lys Asn Glu Gln Glu Leu Leu Glu Leu Asp Lys Trp Ala
        115                 120                 125
```

```
Ser Leu Trp Asn Trp Phe Asn Ile Thr Asn
    130                 135
```

<210> SEQ ID NO 25
<211> LENGTH: 138
<212> TYPE: PRT
<213> ORGANISM: Human

<400> SEQUENCE: 25

```
Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
             20                  25                  30

Gly Ile Lys Gln Leu Gln Ala Arg Ile Leu Ala Val Glu Arg Tyr Leu
         35                  40                  45

Lys Asp Gln Gln Leu Leu Gly Ile Trp Gly Cys Ser Gly Lys Leu Ile
     50                  55                  60

Cys Thr Thr Ala Val Pro Trp Asn Ala Ser Trp Ser Asn Lys Ser Leu
 65                  70                  75                  80

Glu Gln Phe Trp Asn Asn Met Thr Trp Met Glu Trp Asp Arg Glu Ile
                 85                  90                  95

Asn Asn Tyr Thr Ser Leu Ile His Ser Leu Ile Asp Glu Ser Gln Asn
            100                 105                 110

Gln Gln Glu Lys Asn Glu Gln Glu Leu Leu Glu Leu Asp Lys Trp Ala
        115                 120                 125

Ser Leu Trp Asn Trp Phe Asn Ile Thr Asn
    130                 135
```

<210> SEQ ID NO 26
<211> LENGTH: 138
<212> TYPE: PRT
<213> ORGANISM: Human

<400> SEQUENCE: 26

```
Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
             20                  25                  30

Gly Ile Lys Gln Leu Gln Ala Arg Ile Leu Ala Val Glu Arg Tyr Leu
         35                  40                  45

Lys Asp Gln Gln Leu Leu Gly Ile Trp Gly Cys Ser Gly Lys Leu Ile
     50                  55                  60

Cys Thr Thr Ala Val Pro Trp Asn Ala Ser Trp Ser Asn Lys Ser Leu
 65                  70                  75                  80

Glu Gln Ile Trp Asn Asn Met Thr Trp Met Glu Trp Asp Arg Glu Ile
                 85                  90                  95

Asn Asn Tyr Thr Ser Leu Ile His Ser Leu Ile Glu Glu Ser Gln Asn
            100                 105                 110

Gln Gln Glu Lys Asn Glu Gln Glu Leu Leu Glu Leu Asp Lys Trp Ala
        115                 120                 125

Ser Leu Trp Asn Trp Phe Asn Ile Thr Asn
    130                 135
```

<210> SEQ ID NO 27
<211> LENGTH: 138
<212> TYPE: PRT
<213> ORGANISM: Human

```
<400> SEQUENCE: 27

Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
             20                  25                  30

Gly Ile Lys Gln Leu Gln Ala Arg Val Leu Ala Val Glu Arg Tyr Leu
         35                  40                  45

Arg Asp Gln Gln Leu Leu Gly Ile Trp Gly Cys Ser Gly Lys Leu Ile
     50                  55                  60

Cys Thr Thr Thr Val Pro Trp Asn Ala Ser Trp Ser Asn Lys Ser Met
 65                  70                  75                  80

Asp Gln Ile Trp Asn Asn Met Thr Trp Met Glu Trp Glu Arg Glu Ile
                 85                  90                  95

Asp Asn Tyr Thr Ser Leu Ile Tyr Asn Leu Ile Glu Glu Ser Gln Asn
             100                 105                 110

Gln Gln Glu Lys Asn Glu Gln Glu Leu Leu Glu Leu Asp Lys Trp Ala
         115                 120                 125

Ser Leu Trp Asn Trp Phe Ser Ile Thr Asn
    130                 135

<210> SEQ ID NO 28
<211> LENGTH: 138
<212> TYPE: PRT
<213> ORGANISM: Human

<400> SEQUENCE: 28

Gln Ala Arg Gln Leu Leu Ser Gly Ile Val Gln Gln Gln Asn Asn Leu
  1               5                  10                  15

Leu Arg Ala Ile Asp Ala Gln Gln His Leu Leu Gln Leu Thr Val Trp
             20                  25                  30

Gly Ile Lys Gln Leu Gln Ala Arg Val Leu Ala Val Glu Arg Tyr Leu
         35                  40                  45

Arg Asp Gln Gln Leu Leu Gly Ile Trp Gly Cys Ser Gly Lys Leu Ile
     50                  55                  60

Cys Thr Thr Thr Val Pro Trp Asn Ala Ser Trp Ser Asn Lys Ser Met
 65                  70                  75                  80

Asn Gln Ile Trp Asp Asn Leu Thr Trp Met Glu Trp Glu Arg Glu Ile
                 85                  90                  95

Asp Asn Tyr Thr Ser Ile Ile Tyr Ser Leu Ile Glu Glu Ser Gln Asn
             100                 105                 110

Gln Gln Gly Lys Asn Glu Gln Glu Leu Leu Glu Leu Asp Lys Trp Ala
         115                 120                 125

Ser Leu Trp Asn Trp Phe Asp Ile Thr Asn
    130                 135

<210> SEQ ID NO 29
<211> LENGTH: 138
<212> TYPE: PRT
<213> ORGANISM: Human

<400> SEQUENCE: 29

Gln Ala Arg Arg Leu Leu Ser Gly Ile Val Gln Gln Gln Asn Asn Leu
  1               5                  10                  15

Leu Arg Ala Ile Glu Ala Gln Gln His Leu Leu Lys Leu Thr Val Trp
             20                  25                  30
```

```
Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Ile Ile
 50                  55                  60

Cys Pro Thr Asn Val Pro Trp Asn Ser Ser Trp Ser Asn Lys Ser Gln
 65                  70                  75                  80

Ser Asp Ile Trp Asp Lys Met Thr Trp Leu Glu Trp Asp Lys Glu Val
                 85                  90                  95

Ser Asn Tyr Thr Gln Val Ile Tyr Asn Leu Ile Glu Glu Ser Gln Thr
                100                 105                 110

Gln Gln Glu Ile Asn Glu Arg Asp Leu Leu Ala Leu Asp Lys Trp Ala
            115                 120                 125

Asn Leu Trp Asn Trp Phe Asp Ile Ser Asn
130                 135

<210> SEQ ID NO 30
<211> LENGTH: 134
<212> TYPE: PRT
<213> ORGANISM: Human

<400> SEQUENCE: 30

Gln Ser Arg Thr Leu Leu Ala Gly Ile Val Gln Gln Gln Gln Gln Leu
 1               5                  10                  15

Leu Asp Val Val Lys Arg Gln Gln Glu Met Leu Arg Leu Thr Val Trp
                20                  25                  30

Gly Thr Lys Asn Leu Gln Ala Arg Val Thr Ala Ile Glu Lys Tyr Leu
        35                  40                  45

Lys Asp Gln Ala Gln Leu Asn Ser Trp Gly Cys Ala Phe Arg Gln Val
 50                  55                  60

Cys His Thr Thr Val Pro Trp Val Asn Asp Ser Leu Thr Pro Asp Trp
 65                  70                  75                  80

Asn Asn Met Thr Trp Gln Glu Trp Glu Lys Arg Val His Tyr Leu Glu
                 85                  90                  95

Ala Asn Ile Ser Gln Ser Leu Glu Gln Ala Gln Ile Gln Gln Glu Lys
                100                 105                 110

Asn Met Tyr Glu Leu Gln Lys Leu Asn Ser Trp Asp Val Phe Gly Asn
            115                 120                 125

Trp Phe Asp Leu Thr Ser
130

<210> SEQ ID NO 31
<211> LENGTH: 134
<212> TYPE: PRT
<213> ORGANISM: Human

<400> SEQUENCE: 31

Gln Ser Arg Thr Leu Leu Ala Gly Ile Val Gln Gln Gln Gln Gln Leu
 1               5                  10                  15

Leu Asp Val Val Lys Arg Gln Gln Glu Met Leu Arg Leu Thr Val Trp
                20                  25                  30

Gly Thr Lys Asn Leu Gln Ala Arg Val Thr Ala Ile Glu Lys Tyr Leu
        35                  40                  45

Lys Asp Gln Ala Gln Leu Asn Ser Trp Gly Cys Ala Phe Arg Gln Val
 50                  55                  60

Cys His Thr Thr Val Pro Trp Val Asn Asp Ser Leu Ser Pro Asp Trp
 65                  70                  75                  80
```

```
Asn Asn Met Thr Trp Gln Glu Trp Glu Lys Gln Val Arg Tyr Leu Glu
             85                  90                  95

Ala Asn Ile Ser Gln Ser Leu Glu Gln Ala Gln Ile Gln Gln Glu Lys
            100                 105                 110

Asn Met Tyr Glu Leu Gln Lys Leu Asn Ser Trp Asp Val Phe Gly Asn
            115                 120                 125

Trp Phe Asp Leu Thr Ser
        130

<210> SEQ ID NO 32
<211> LENGTH: 134
<212> TYPE: PRT
<213> ORGANISM: Human

<400> SEQUENCE: 32

Gln Ser Arg Thr Leu Leu Ala Gly Ile Val Gln Gln Gln Gln Gln Leu
  1               5                  10                  15

Leu Asp Val Val Lys Arg Gln Gln Glu Met Leu Arg Leu Thr Val Trp
             20                  25                  30

Gly Thr Lys Asn Leu Gln Ala Arg Val Thr Ala Ile Glu Lys Tyr Leu
         35                  40                  45

Lys His Gln Ala Gln Leu Asn Ser Trp Gly Cys Ala Phe Arg Gln Val
     50                  55                  60

Cys His Thr Thr Val Pro Trp Val Asn Asp Ser Leu Ser Pro Asp Trp
 65                  70                  75                  80

Lys Asn Met Thr Trp Gln Glu Trp Glu Lys Gln Val Arg Tyr Leu Glu
             85                  90                  95

Ala Asn Ile Ser Gln Ser Leu Glu Gln Ala Gln Ile Gln Gln Glu Lys
            100                 105                 110

Asn Met Tyr Glu Leu Gln Lys Leu Asn Ser Trp Asp Ile Leu Gly Asn
            115                 120                 125

Trp Phe Asp Leu Thr Ser
        130

<210> SEQ ID NO 33
<211> LENGTH: 134
<212> TYPE: PRT
<213> ORGANISM: Human

<400> SEQUENCE: 33

Gln Ser Arg Thr Leu Leu Ala Gly Ile Val Gln Gln Gln Gln Gln Leu
  1               5                  10                  15

Leu Asp Val Val Lys Arg Gln Gln Glu Met Leu Arg Leu Thr Val Trp
             20                  25                  30

Gly Thr Lys Asn Leu Gln Ala Arg Val Thr Ala Ile Glu Lys Tyr Leu
         35                  40                  45

Lys Asp Gln Ala Gln Leu Asn Ser Trp Gly Cys Ala Phe Arg Gln Val
     50                  55                  60

Cys His Thr Ser Val Pro Trp Val Asn Asp Thr Leu Thr Pro Asp Trp
 65                  70                  75                  80

Asn Asn Met Thr Trp Gln Glu Trp Glu Gln Lys Val Arg Tyr Leu Glu
             85                  90                  95

Ala Asn Ile Ser Gln Ser Leu Glu Gln Ala Gln Ile Gln Gln Glu Lys
            100                 105                 110

Asn Met Tyr Glu Leu Gln Lys Leu Asn Ser Trp Asp Val Phe Thr Asn
            115                 120                 125
```

Trp Leu Asp Phe Thr Ser
    130

<210> SEQ ID NO 34
<211> LENGTH: 134
<212> TYPE: PRT
<213> ORGANISM: Human

<400> SEQUENCE: 34

Gln Ser Arg Thr Leu Leu Ala Gly Ile Val Gln Gln Gln Gln Gln Leu
 1               5                  10                  15

Leu Asp Val Val Lys Arg Gln Gln Glu Leu Leu Arg Leu Thr Val Trp
            20                  25                  30

Gly Thr Lys Ile Leu Gln Ala Arg Val Thr Ala Ile Glu Lys Tyr Leu
        35                  40                  45

Lys Asp Gln Ala Gln Leu Asn Ser Trp Gly Cys Ala Phe Arg Gln Val
    50                  55                  60

Cys His Thr Thr Val Pro Trp Ala Asn Glu Ser Leu Thr Pro Asp Trp
65                  70                  75                  80

Asn Asn Met Thr Trp Gln Glu Trp Glu Gln Lys Val Arg Tyr Leu Glu
                85                  90                  95

Ala Asn Ile Ser Gln Ser Leu Glu Glu Ala Gln Leu Gln Gln Glu Lys
            100                 105                 110

Asn Met Tyr Glu Leu Gln Lys Leu Asn Asn Trp Asp Val Phe Thr Asn
        115                 120                 125

Trp Phe Asp Leu Thr Ser
    130

<210> SEQ ID NO 35
<211> LENGTH: 134
<212> TYPE: PRT
<213> ORGANISM: Human

<400> SEQUENCE: 35

Gln Ser Arg Thr Leu Leu Ala Gly Ile Val Gln Gln Gln Gln Gln Leu
 1               5                  10                  15

Leu Asp Val Val Lys Arg Gln Gln Glu Leu Leu Arg Leu Thr Val Trp
            20                  25                  30

Gly Thr Lys Asn Leu Gln Ala Arg Val Thr Ala Ile Glu Lys Tyr Leu
        35                  40                  45

Gln Asp Gln Ala Arg Leu Asn Ser Trp Gly Cys Ala Phe Arg Gln Val
    50                  55                  60

Cys His Thr Thr Val Pro Trp Val Asn Asp Ser Leu Ala Pro Asp Trp
65                  70                  75                  80

Asp Asn Met Thr Trp Gln Glu Trp Glu Lys Gln Val Arg Tyr Leu Glu
                85                  90                  95

Ala Asn Ile Ser Lys Ser Leu Glu Gln Ala Gln Ile Gln Gln Glu Lys
            100                 105                 110

Asn Met Tyr Glu Leu Gln Lys Leu Asn Ser Trp Asp Ile Phe Gly Asn
        115                 120                 125

Trp Phe Asp Leu Thr Ser
    130

<210> SEQ ID NO 36
<211> LENGTH: 134
<212> TYPE: PRT
<213> ORGANISM: Human

<400> SEQUENCE: 36

Gln Ser Arg Thr Ser Leu Ala Gly Ile Val Gln Gln Gln Gln Leu
1               5                   10                  15

Leu Asp Val Val Lys Arg Gln Gln Glu Met Leu Arg Leu Thr Val Trp
                20                  25                  30

Gly Thr Lys Asn Leu Gln Ala Arg Val Thr Ala Ile Glu Lys Tyr Leu
            35                  40                  45

Lys Asp Gln Ala Gln Leu Asn Ser Trp Gly Cys Ala Phe Arg Gln Val
        50                  55                  60

Cys His Thr Thr Val Pro Trp Val Asn Asp Thr Leu Thr Pro Asp Trp
65                  70                  75                  80

Asn Asn Ile Thr Trp Gln Glu Trp Glu Gln Arg Ile Arg Asn Leu Glu
                85                  90                  95

Ala Asn Ile Ser Glu Ser Leu Glu Gln Ala Gln Ile Gln Gln Glu Lys
            100                 105                 110

Asn Met Tyr Glu Leu Gln Lys Leu Asn Ser Trp Asp Val Phe Ser Asn
        115                 120                 125

Trp Phe Asp Leu Thr Ser
    130

<210> SEQ ID NO 37
<211> LENGTH: 134
<212> TYPE: PRT
<213> ORGANISM: Human

<400> SEQUENCE: 37

Gln Ser Arg Thr Leu Leu Ala Gly Ile Val Gln Gln Gln Gln Leu
1               5                   10                  15

Leu Asp Val Val Lys Arg Gln Gln Glu Met Leu Arg Leu Thr Val Trp
                20                  25                  30

Gly Thr Lys Asn Leu Gln Ala Arg Val Thr Ala Ile Glu Lys Tyr Leu
            35                  40                  45

Lys Asp Gln Ala Gln Leu Asn Ser Trp Gly Cys Ala Phe Arg Gln Val
        50                  55                  60

Cys His Thr Thr Val Pro Trp Val Asn Asp Thr Leu Thr Pro Asp Trp
65                  70                  75                  80

Asn Asn Met Thr Trp Gln Glu Trp Glu Gln Arg Ile Arg Asn Leu Glu
                85                  90                  95

Ala Asn Ile Ser Glu Ser Leu Glu Gln Ala Gln Ile Gln Gln Glu Lys
            100                 105                 110

Asn Met Tyr Glu Leu Gln Lys Leu Asn Ser Trp Asp Val Phe Gly Asn
        115                 120                 125

Trp Phe Asp Leu Thr Ser
    130

<210> SEQ ID NO 38
<211> LENGTH: 134
<212> TYPE: PRT
<213> ORGANISM: Human

<400> SEQUENCE: 38

Gln Ser Arg Thr Leu Phe Arg Gly Ile Val Gln Gln Gln Gln Leu
1               5                   10                  15

Leu Asp Val Val Lys Arg Gln Gln Glu Met Leu Arg Leu Thr Val Trp
                20                  25                  30

Gly Thr Lys Asn Leu Gln Ala Arg Val Thr Ala Ile Glu Lys Tyr Leu

-continued

```
                35                  40                  45
Ala Asp Gln Ala Arg Leu Asn Ser Trp Gly Cys Ala Phe Arg Gln Val
    50                  55                  60
Cys His Thr Thr Val Pro Trp Val Asn Asp Thr Leu Thr Pro Glu Trp
 65                  70                  75                  80
Asn Asn Met Thr Trp Gln Glu Trp Glu His Lys Ile Arg Phe Leu Glu
                85                  90                  95
Ala Asn Ile Ser Glu Ser Leu Glu Gln Ala Gln Ile Gln Gln Glu Lys
               100                 105                 110
Asn Met Tyr Glu Leu Gln Lys Leu Asn Ser Trp Asp Val Phe Gly Asn
           115                 120                 125
Trp Phe Asp Leu Thr Ser
        130
```

<210> SEQ ID NO 39
<211> LENGTH: 134
<212> TYPE: PRT
<213> ORGANISM: Human

<400> SEQUENCE: 39

```
Gln Ser Arg Thr Leu Leu Ala Gly Ile Val Gln Gln Gln Gln Gln Pro
  1               5                  10                  15
Val Asp Val Val Lys Arg Gln Gln Glu Leu Leu Arg Leu Thr Val Trp
             20                  25                  30
Gly Thr Lys Asn Leu Gln Ala Arg Val Thr Ala Ile Glu Lys Tyr Leu
            35                  40                  45
Lys Asp Gln Ala Gln Leu Asn Ser Trp Gly Cys Ala Phe Arg Gln Val
    50                  55                  60
Cys His Thr Thr Val Pro Trp Pro Asn Glu Thr Leu Thr Pro Asn Trp
 65                  70                  75                  80
Asn Asn Met Thr Trp Gln Gln Trp Glu Lys Gln Val His Phe Leu Asp
                85                  90                  95
Ala Asn Ile Thr Ala Leu Leu Glu Glu Ala Gln Ile Gln Gln Glu Lys
               100                 105                 110
Asn Met Tyr Glu Leu Gln Lys Ile Asn Ser Trp Asp Val Phe Gly Asn
           115                 120                 125
Trp Phe Asp Leu Thr Ser
        130
```

<210> SEQ ID NO 40
<211> LENGTH: 142
<212> TYPE: PRT
<213> ORGANISM: Feline immunodeficiency virus

<400> SEQUENCE: 40

```
Gln Tyr His Gln Val Leu Ala Thr His Gln Glu Ala Ile Glu Lys Val
  1               5                  10                  15
Thr Gly Ala Leu Lys Ile Asn Asn Leu Arg Leu Val Thr Leu Glu His
             20                  25                  30
Gln Val Leu Val Ile Gly Leu Lys Val Glu Ala Met Glu Lys Phe Leu
            35                  40                  45
Tyr Thr Ala Phe Ala Met Gln Glu Leu Gly Cys Asn Gln Asn Gln Phe
    50                  55                  60
Phe Cys Lys Ile Pro Leu Glu Leu Trp Thr Arg Tyr Asn Met Thr Ile
 65                  70                  75                  80
Asn Gln Thr Ile Trp Asn His Gly Asn Ile Thr Leu Gly Glu Trp Tyr
```

```
                     85                  90                  95
Asn Gln Thr Lys Asp Leu Gln Gln Lys Phe Tyr Glu Ile Ile Met Asp
                100                 105                 110

Ile Glu Gln Asn Asn Val Gln Gly Lys Thr Gly Ile Gln Gln Leu Gln
            115                 120                 125

Lys Trp Glu Asp Trp Val Arg Trp Ile Gly Asn Ile Pro Gln
130                 135                 140

<210> SEQ ID NO 41
<211> LENGTH: 142
<212> TYPE: PRT
<213> ORGANISM: Feline immunodeficiency virus

<400> SEQUENCE: 41

Gln Tyr His Gln Val Leu Ala Thr Gln Glu Ala Ile Glu Lys Val
  1               5                  10                  15

Thr Glu Ala Leu Lys Ile Thr Asn Leu Arg Leu Val Thr Leu Glu His
             20                  25                  30

Gln Val Leu Val Ile Gly Leu Lys Val Glu Ala Met Glu Lys Phe Leu
         35                  40                  45

Tyr Thr Ala Phe Ala Met Gln Glu Leu Gly Cys Asn Gln Asn Gln Phe
     50                  55                  60

Phe Cys Lys Val Pro Pro Glu Leu Trp Arg Arg Tyr Asn Met Thr Ile
 65                  70                  75                  80

Asn Gln Thr Ile Trp Asn His Gly Asn Ile Thr Leu Gly Glu Trp Tyr
                 85                  90                  95

Asn Gln Thr Lys Asp Leu Gln Lys Phe Tyr Gly Ile Ile Met Asp
                100                 105                 110

Ile Glu Gln Asn Asn Val Gln Gly Lys Lys Gly Leu Gln Gln Leu Gln
            115                 120                 125

Lys Trp Glu Asp Trp Val Gly Trp Ile Gly Asn Ile Pro Gln
130                 135                 140

<210> SEQ ID NO 42
<211> LENGTH: 142
<212> TYPE: PRT
<213> ORGANISM: Feline immunodeficiency virus

<400> SEQUENCE: 42

Gln Tyr Gln Gln Val Leu Ala Thr His Gln Glu Ala Ile Glu Lys Val
  1               5                  10                  15

Thr Glu Ala Leu Lys Ile Asn Asn Leu Arg Leu Val Thr Leu Glu His
             20                  25                  30

Gln Val Leu Val Ile Gly Leu Lys Val Glu Ala Met Glu Lys Phe Leu
         35                  40                  45

Tyr Thr Ala Phe Ala Met Gln Glu Leu Gly Cys Asn Gln Asn Gln Phe
     50                  55                  60

Phe Cys Lys Val Pro Ser Ala Leu Trp Glu Arg Tyr Asn Met Thr Ile
 65                  70                  75                  80

Asn Gln Thr Ile Trp Asn His Gly Asn Ile Thr Leu Gly Glu Trp Tyr
                 85                  90                  95

Asn Gln Thr Lys Asp Leu Gln Arg Phe Tyr Glu Ile Ile Met Asp
                100                 105                 110

Ile Glu Gln Asn Asn Val Gln Gly Lys Lys Gly Leu Gln Gln Leu Gln
            115                 120                 125

Glu Trp Glu Asp Trp Val Gly Trp Ile Gly Asn Ile Pro Gln
```

```
              130                 135                 140

<210> SEQ ID NO 43
<211> LENGTH: 142
<212> TYPE: PRT
<213> ORGANISM: Feline immunodeficiency virus

<400> SEQUENCE: 43

Gln Tyr His Gln Val Leu Ala Thr His Gln Glu Thr Ile Glu Lys Ile
  1               5                  10                  15

Thr Glu Ala Leu Lys Val Asn Asn Leu Arg Leu Val Thr Leu Glu His
             20                  25                  30

Gln Val Leu Val Ile Gly Leu Lys Val Glu Ala Ile Glu Lys Phe Leu
         35                  40                  45

Tyr Thr Ala Phe Ala Met Gln Glu Leu Gly Cys Asn Gln Asn Gln Phe
     50                  55                  60

Phe Cys Lys Val Pro Pro Glu Leu Trp Gln Arg Tyr Asn Met Thr Ile
 65                  70                  75                  80

Asn Gln Thr Ile Trp Asn His Gly Asn Ile Thr Leu Gly Glu Trp Tyr
                 85                  90                  95

Asn Gln Thr Lys Asp Leu Gln Gln Lys Phe Tyr Glu Ile Ile Met Asp
            100                 105                 110

Met Glu Gln Asn Asn Val Gln Gly Arg Lys Gly Leu Gln Gln Leu Gln
        115                 120                 125

Glu Trp Glu Asp Trp Val Gly Trp Leu Gly Asn Ile Pro Arg
    130                 135                 140

<210> SEQ ID NO 44
<211> LENGTH: 142
<212> TYPE: PRT
<213> ORGANISM: Feline immunodeficiency virus

<400> SEQUENCE: 44

Gln Tyr His Gln Val Leu Ala Thr His Gln Glu Thr Ile Glu Lys Val
  1               5                  10                  15

Thr Glu Ala Leu Lys Ile Asn Asn Leu Arg Leu Val Thr Leu Glu His
             20                  25                  30

Gln Val Leu Val Ile Gly Leu Lys Val Glu Ala Met Glu Lys Phe Leu
         35                  40                  45

Tyr Thr Ala Phe Ala Met Gln Glu Leu Gly Cys Asn Gln Asn Gln Phe
     50                  55                  60

Phe Cys Lys Val Pro Pro Glu Leu Trp Lys Arg Tyr Asn Met Thr Ile
 65                  70                  75                  80

Asn Gln Thr Ile Trp Asn His Gly Asn Ile Thr Leu Gly Glu Trp Tyr
                 85                  90                  95

Asn Gln Thr Lys Glu Leu Gln Gln Lys Phe Tyr Glu Ile Ile Met Asn
            100                 105                 110

Ile Glu Gln Asn Asn Val Gln Val Lys Lys Gly Leu Gln Gln Leu Gln
        115                 120                 125

Glu Trp Glu Asp Trp Val Gly Trp Ile Gly Asn Ile Pro Gln
    130                 135                 140

<210> SEQ ID NO 45
<211> LENGTH: 142
<212> TYPE: PRT
<213> ORGANISM: Feline immunodeficiency virus

<400> SEQUENCE: 45
```

```
Gln Tyr Gln Gln Val Leu Ala Thr His Gln Glu Ala Leu Asp Lys Ile
 1               5                  10                  15

Thr Glu Ala Leu Lys Ile Asn Asn Leu Arg Leu Val Thr Leu Glu His
            20                  25                  30

Gln Met Leu Val Ile Gly Leu Lys Val Glu Ala Ile Glu Lys Phe Leu
            35                  40                  45

Tyr Thr Ala Phe Ala Met Gln Glu Leu Gly Cys Asn Gln Asn Gln Phe
 50                  55                  60

Phe Cys Glu Ile Pro Lys Glu Leu Trp Leu Arg Tyr Asn Met Thr Leu
 65                  70                  75                  80

Asn Gln Thr Ile Trp Asn His Gly Asn Ile Thr Leu Gly Glu Trp Tyr
            85                  90                  95

Asn Gln Thr Lys Tyr Leu Gln Gln Lys Phe Tyr Glu Ile Ile Met Asp
            100                 105                 110

Ile Glu Gln Asn Asn Val Gln Gly Lys Gln Gly Leu Gln Lys Leu Gln
            115                 120                 125

Asn Trp Gln Asp Trp Met Gly Trp Ile Gly Lys Ile Pro Gln
            130                 135                 140

<210> SEQ ID NO 46
<211> LENGTH: 142
<212> TYPE: PRT
<213> ORGANISM: Feline immunodeficiency virus

<400> SEQUENCE: 46

Gln Tyr His Gln Val Leu Ala Thr His Gln Ala Leu Glu Lys Ile
 1               5                  10                  15

Thr Glu Ala Leu Lys Ile Asn Asn Leu Arg Leu Ile Thr Leu Glu His
            20                  25                  30

Gln Val Leu Val Ile Gly Leu Arg Val Glu Ala Ile Glu Lys Phe Leu
            35                  40                  45

Tyr Thr Ala Phe Ala Met Gln Glu Leu Gly Cys Asn Gln Asn Gln Phe
 50                  55                  60

Phe Cys Lys Ile Pro Pro Ser Leu Trp Ser Met Tyr Asn Met Thr Leu
 65                  70                  75                  80

Asn Gln Thr Ile Trp Asn His Gly Asn Ile Ser Leu Gly Asn Trp Tyr
            85                  90                  95

Asn Gln Thr Arg Asp Leu Gln Asn Lys Phe Tyr Glu Ile Ile Met Asp
            100                 105                 110

Ile Glu Gln Asn Asn Val Gln Gly Lys Thr Gly Ile Gln Gln Leu Gln
            115                 120                 125

Lys Trp Glu Asn Trp Val Gly Trp Ile Gly Lys Ile Pro Gln
            130                 135                 140

<210> SEQ ID NO 47
<211> LENGTH: 134
<212> TYPE: PRT
<213> ORGANISM: Simian immunodeficiency virus

<400> SEQUENCE: 47

Gln Ser Arg Thr Leu Leu Ala Gly Ile Val Gln Gln Gln Gln Gln Leu
 1               5                  10                  15

Leu Gly Val Val Lys Arg Gln Gln Glu Leu Leu Arg Leu Thr Val Trp
            20                  25                  30

Gly Thr Lys Asn Leu Gln Thr Arg Val Thr Ala Ile Glu Lys Tyr Leu
            35                  40                  45
```

```
Glu Asp Gln Ala Gln Leu Asn Ala Trp Gly Cys Ala Phe Arg Gln Val
 50                  55                  60

Cys His Thr Thr Val Pro Trp Pro Asn Ala Ser Leu Thr Pro Asp Trp
 65                  70                  75                  80

Asn Asn Asp Thr Trp Gln Glu Trp Glu Arg Lys Val Asp Phe Leu Glu
                 85                  90                  95

Glu Asn Ile Thr Ala Leu Leu Glu Glu Ala Gln Ile Gln Gln Glu Lys
            100                 105                 110

Asn Met Tyr Glu Leu Gln Lys Leu Asn Ser Trp Asp Val Phe Gly Asn
            115                 120                 125

Trp Phe Asp Leu Ala Ser
        130

<210> SEQ ID NO 48
<211> LENGTH: 134
<212> TYPE: PRT
<213> ORGANISM: Simian immunodeficiency virus

<400> SEQUENCE: 48

Gln Ser Arg Thr Leu Leu Ala Gly Ile Val Gln Gln Gln Gln Gln Leu
  1               5                  10                  15

Leu Asp Val Val Lys Arg Gln Gln Glu Leu Leu Arg Leu Thr Val Trp
                 20                  25                  30

Gly Thr Lys Asn Leu Gln Thr Lys Val Thr Ala Ile Glu Lys Tyr Leu
             35                  40                  45

Lys Asp Gln Ala Gln Leu Asn Ala Trp Gly Cys Ala Phe Arg Gln Val
 50                  55                  60

Cys His Ile Thr Val Pro Trp Pro Asn Ala Ser Leu Thr Pro Asp Trp
 65                  70                  75                  80

Asn Asn Asp Thr Trp Gln Glu Trp Glu Arg Lys Val Asp Phe Leu Glu
                 85                  90                  95

Glu Asn Ile Thr Ala Leu Leu Glu Glu Ala Gln Ile Gln Gln Glu Lys
            100                 105                 110

Asn Met Tyr Lys Leu Gln Lys Leu Asn Ser Trp Asp Val Phe Gly Asn
            115                 120                 125

Trp Phe Asp Leu Ala Ser
        130

<210> SEQ ID NO 49
<211> LENGTH: 134
<212> TYPE: PRT
<213> ORGANISM: Simian immunodeficiency virus

<400> SEQUENCE: 49

Gln Ser Arg Thr Leu Leu Ala Gly Ile Val Gln Gln Gln Gln Gln Leu
  1               5                  10                  15

Leu Asp Val Val Lys Arg Gln Gln Glu Leu Leu Arg Leu Thr Val Trp
                 20                  25                  30

Gly Thr Lys Asn Leu Gln Thr Arg Val Ser Ala Ile Glu Lys Tyr Leu
             35                  40                  45

Lys Asp Gln Ala Gln Leu Asn Ala Trp Gly Cys Ala Phe Arg Gln Val
 50                  55                  60

Cys His Thr Thr Val Pro Trp Pro Asn Ala Ser Leu Thr Pro Asp Trp
 65                  70                  75                  80

Asn Asn Glu Thr Trp Gln Glu Trp Glu Arg Lys Val Asp Phe Leu Glu
                 85                  90                  95
```

-continued

```
Ala Asn Ile Thr Ala Leu Leu Glu Glu Ala Gln Ile Gln Gln Glu Lys
            100                 105                 110

Asn Met Tyr Glu Leu Gln Lys Leu Asn Ser Trp Asp Val Phe Gly Asn
            115                 120                 125

Trp Phe Asp Leu Thr Ser
    130
```

<210> SEQ ID NO 50
<211> LENGTH: 134
<212> TYPE: PRT
<213> ORGANISM: Simian immunodeficiency virus

<400> SEQUENCE: 50

```
Gln Ser Arg Thr Leu Leu Ala Gly Ile Val Gln Gln Gln Gln Gln Leu
  1               5                  10                  15

Leu Asp Val Val Lys Arg Gln Gln Glu Leu Leu Arg Leu Thr Val Trp
             20                  25                  30

Gly Thr Lys Asn Leu Gln Thr Arg Val Thr Ala Ile Glu Lys Tyr Leu
             35                  40                  45

Lys Asp Gln Ala Gln Leu Asn Ser Trp Gly Cys Ala Phe Arg Gln Val
  50                  55                  60

Cys His Thr Thr Val Pro Trp Pro Asn Glu Thr Leu Val Pro Asn Trp
 65                  70                  75                  80

Asn Asn Met Thr Trp Gln Glu Trp Glu Arg Gln Val Asp Phe Leu Glu
             85                  90                  95

Ala Asn Ile Thr Gln Leu Leu Glu Glu Ala Gln Ile Gln Gln Glu Lys
            100                 105                 110

Asn Met Tyr Glu Leu Gln Lys Leu Asn Ser Trp Asp Ile Phe Gly Asn
            115                 120                 125

Trp Phe Asp Leu Thr Ser
    130
```

<210> SEQ ID NO 51
<211> LENGTH: 134
<212> TYPE: PRT
<213> ORGANISM: Simian immunodeficiency virus

<400> SEQUENCE: 51

```
Gln Ser Arg Thr Leu Leu Ala Gly Ile Val Gln Gln Gln Gln Gln Leu
  1               5                  10                  15

Leu Asp Val Val Lys Arg Gln Gln Glu Leu Leu Arg Leu Thr Val Trp
             20                  25                  30

Gly Ala Lys Asn Leu Gln Thr Arg Val Thr Ala Ile Glu Lys Tyr Leu
             35                  40                  45

Lys Asp Gln Ala Gln Leu Asn Ser Trp Gly Cys Ala Phe Arg Gln Val
  50                  55                  60

Cys His Thr Thr Val Pro Arg Pro Asn Asp Thr Leu Thr Pro Asn Trp
 65                  70                  75                  80

Asn Asn Met Thr Trp Gln Glu Trp Glu Lys Gln Val Asn Phe Leu Glu
             85                  90                  95

Ala Asn Ile Thr Gln Ser Leu Glu Glu Ala Gln Ile Gln Gln Glu Lys
            100                 105                 110

Asn Thr Tyr Glu Leu Gln Lys Leu Asn Ser Trp Asp Ile Phe Gly Asn
            115                 120                 125

Trp Phe Asp Leu Thr Ser
    130
```

<210> SEQ ID NO 52
<211> LENGTH: 134
<212> TYPE: PRT
<213> ORGANISM: Simian immunodeficiency virus

<400> SEQUENCE: 52

Gln Ser Gln His Leu Leu Ala Gly Ile Leu Gln Gln Gln Lys Asn Leu
 1               5                  10                  15

Leu Ala Ala Val Glu Ala Gln Gln Met Leu Lys Leu Thr Ile Trp
            20                  25                  30

Gly Val Lys Asn Leu Asn Ala Arg Val Thr Ala Leu Glu Lys Tyr Leu
            35                  40                  45

Glu Asp Gln Ala Arg Leu Asn Ala Trp Gly Cys Ala Trp Lys Gln Val
        50                  55                  60

Cys His Thr Thr Val Pro Trp Gln Trp Asn Asn Arg Thr Pro Asp Trp
65                  70                  75                  80

Asn Asn Met Thr Trp Leu Glu Trp Glu Arg Gln Ile Ser Tyr Leu Glu
                85                  90                  95

Gly Asn Ile Thr Thr Gln Leu Glu Glu Ala Arg Ala Gln Glu Glu Lys
            100                 105                 110

Asn Leu Asp Ala Tyr Gln Lys Leu Ser Ser Trp Ser Asp Phe Trp Ser
        115                 120                 125

Trp Phe Asp Phe Ser Lys
        130

<210> SEQ ID NO 53
<211> LENGTH: 134
<212> TYPE: PRT
<213> ORGANISM: Simian immunodeficiency virus

<400> SEQUENCE: 53

Gln Ser Arg His Leu Leu Ala Gly Ile Leu Gln Gln Gln Lys Asn Leu
 1               5                  10                  15

Leu Ala Ala Val Glu Ala Gln Gln Met Leu Lys Leu Thr Ile Trp
            20                  25                  30

Gly Val Lys Asn Leu Asn Ala Arg Val Thr Ala Leu Glu Lys Tyr Leu
            35                  40                  45

Glu Asp Gln Ala Arg Leu Asn Ser Trp Gly Cys Ala Trp Lys Gln Val
        50                  55                  60

Cys His Thr Thr Val Glu Trp Pro Trp Thr Asn Arg Thr Pro Asp Trp
65                  70                  75                  80

Gln Asn Met Thr Trp Leu Glu Trp Glu Arg Gln Ile Ala Asp Leu Glu
                85                  90                  95

Ser Asn Ile Thr Gly Gln Leu Val Lys Ala Arg Glu Gln Glu Glu Lys
            100                 105                 110

Asn Leu Asp Ala Tyr Gln Lys Leu Thr Ser Trp Ser Asp Phe Trp Ser
        115                 120                 125

Trp Phe Asp Phe Ser Lys
        130

<210> SEQ ID NO 54
<211> LENGTH: 133
<212> TYPE: PRT
<213> ORGANISM: Simian immunodeficiency virus

<400> SEQUENCE: 54

```
Gln Ser Gln His Leu Leu Ala Gly Ile Leu Gln Gln Lys Asn Leu
 1               5                  10                  15

Leu Ala Ala Val Gly Ala Gln Gln Met Leu Lys Leu Thr Ile Trp
             20                  25                  30

Gly Val Lys Asn Leu Asn Ala Arg Val Thr Ala Leu Glu Lys Tyr Leu
             35                  40                  45

Ala Asp Gln Ala Arg Leu Asn Ala Trp Gly Cys Ala Trp Lys Gln Val
     50                  55                  60

Cys His Thr Thr Val Pro Trp Thr Trp Asn Asn Thr Pro Glu Trp Asn
 65                  70                  75                  80

Asn Met Thr Trp Leu Glu Trp Glu Lys Gln Ile Glu Gly Leu Glu Gly
                 85                  90                  95

Asn Ile Thr Lys Gln Leu Glu Gln Ala Arg Glu Gln Glu Glu Lys Asn
             100                 105                 110

Leu Asp Ala Tyr Gln Lys Leu Ser Asp Trp Ser Ser Phe Trp Ser Trp
         115                 120                 125

Phe Asp Phe Ser Lys
         130

<210> SEQ ID NO 55
<211> LENGTH: 133
<212> TYPE: PRT
<213> ORGANISM: Simian immunodeficiency virus

<400> SEQUENCE: 55

Gln Ser Arg His Leu Leu Ala Gly Ile Leu Gln Gln Lys Asn Leu
 1               5                  10                  15

Leu Ala Ala Val Glu Gln Gln Gln Leu Leu Lys Leu Thr Ile Trp
             20                  25                  30

Gly Val Lys Asn Leu Asn Ala Arg Val Thr Ala Leu Glu Lys Tyr Leu
             35                  40                  45

Glu Asp Gln Ala Arg Leu Asn Ser Trp Gly Cys Ala Trp Lys Gln Val
     50                  55                  60

Cys His Thr Thr Val Pro Trp Lys Tyr Asn Asn Thr Pro Lys Trp Asp
 65                  70                  75                  80

Asn Met Thr Trp Leu Glu Trp Glu Arg Gln Ile Asn Ala Leu Glu Gly
                 85                  90                  95

Asn Ile Thr Gln Leu Leu Glu Glu Ala Gln Asn Gln Glu Ser Lys Asn
             100                 105                 110

Leu Asp Leu Tyr Gln Lys Leu Asp Asp Trp Ser Gly Phe Trp Ser Trp
         115                 120                 125

Phe Ser Leu Ser Thr
         130

<210> SEQ ID NO 56
<211> LENGTH: 134
<212> TYPE: PRT
<213> ORGANISM: Simian immunodeficiency virus

<400> SEQUENCE: 56

Gln Ser Gln Ser Leu Val Thr Gly Ile Val Glu Gln Lys Gln Leu
 1               5                  10                  15

Leu Lys Leu Ile Glu Gln Gln Ser Glu Leu Leu Lys Leu Thr Ile Trp
             20                  25                  30

Gly Val Lys Asn Leu Gln Thr Arg Leu Thr Ser Leu Glu Asn Tyr Ile
             35                  40                  45
```

-continued

Lys Asp Gln Ala Leu Leu Ser Gln Trp Gly Cys Ser Trp Ala Gln Val
 50                  55                  60

Cys His Thr Ser Val Glu Trp Thr Asn Thr Ser Ile Thr Pro Asn Trp
 65                  70                  75                  80

Thr Ser Glu Thr Trp Lys Glu Trp Glu Thr Arg Thr Asp Tyr Leu Gln
                 85                  90                  95

Gln Asn Ile Thr Glu Met Leu Lys Gln Ala Tyr Asp Arg Glu Gln Arg
            100                 105                 110

Asn Thr Tyr Glu Leu Gln Lys Leu Gly Asp Leu Thr Ser Trp Ala Ser
        115                 120                 125

Trp Phe Asp Phe Thr Trp
    130

<210> SEQ ID NO 57
<211> LENGTH: 139
<212> TYPE: PRT
<213> ORGANISM: Simian immunodeficiency virus

<400> SEQUENCE: 57

Gln Ala Arg Gln Leu Leu Ser Gly Ile Val Gln Gln Gln Asn Asn Leu
  1               5                  10                  15

Leu Lys Ala Ile Glu Ala Gln Gln His Leu Leu Gln Leu Ser Ile Trp
                 20                  25                  30

Gly Val Lys Gln Leu Gln Ala Arg Leu Leu Ala Val Glu Arg Tyr Leu
             35                  40                  45

Gln Asp Gln Gln Ile Leu Gly Leu Trp Gly Cys Ser Gly Lys Ala Val
 50                  55                  60

Cys Tyr Thr Thr Val Pro Trp Asn Asn Ser Trp Pro Gly Ser Asn Ser
 65                  70                  75                  80

Thr Asp Asp Ile Trp Gly Asn Leu Thr Trp Gln Gln Trp Asp Lys Leu
                 85                  90                  95

Val Ser Asn Tyr Thr Gly Lys Ile Phe Gly Leu Leu Glu Glu Ala Gln
            100                 105                 110

Ser Gln Gln Glu Lys Asn Glu Arg Asp Leu Leu Glu Leu Asp Gln Trp
        115                 120                 125

Ala Ser Leu Trp Asn Trp Phe Asp Ile Thr Lys
    130                 135

<210> SEQ ID NO 58
<211> LENGTH: 138
<212> TYPE: PRT
<213> ORGANISM: Human

<400> SEQUENCE: 58

Gln Ala Arg Gln Leu Leu Ser Gly Ile Val Gln Gln Gln Asn Asn Leu
  1               5                  10                  15

Leu Arg Ala Ile Glu Ala Gln Gln His Leu Leu Gln Leu Thr Val Trp
                 20                  25                  30

Gly Ile Lys Gln Leu Gln Ala Arg Ile Leu Ala Val Glu Arg Tyr Leu
             35                  40                  45

Lys Asp Gln Gln Leu Leu Gly Ile Trp Gly Cys Ser Gly Lys Leu Ile
 50                  55                  60

Cys Thr Thr Ala Val Pro Trp Asn Ala Ser Trp Ser Asn Lys Ser Leu
 65                  70                  75                  80

Glu Gln Ile Trp Asn Asn Met Thr Trp Met Glu Trp Asp Arg Glu Ile
                 85                  90                  95

```
Asn Asn Tyr Thr Ser Leu Ile His Ser Leu Ile Glu Glu Ser Gln Asn
            100                 105                 110

Gln Gln Glu Lys Asn Glu Gln Glu Leu Leu Glu Leu Asp Lys Trp Ala
            115                 120                 125

Ser Leu Trp Asn Trp Phe Asn Ile Thr Asn
        130                 135

<210> SEQ ID NO 59
<211> LENGTH: 23
<212> TYPE: PRT
<213> ORGANISM: Human

<400> SEQUENCE: 59

Gln Gln Gln Asn Asn Leu Leu Arg Ala Ile Glu Ala Gln Gln His Leu
  1               5                   10                  15

Leu Gln Leu Thr Val Trp Gly
            20

<210> SEQ ID NO 60
<211> LENGTH: 30
<212> TYPE: PRT
<213> ORGANISM: Human

<400> SEQUENCE: 60

Gln Leu Thr Val Trp Gly Ile Lys Gln Leu Gln Ala Arg Ile Leu Ala
  1               5                   10                  15

Val Glu Arg Tyr Leu Lys Asp Gln Gln Leu Leu Gly Ile Trp
            20                  25                  30

<210> SEQ ID NO 61
<211> LENGTH: 31
<212> TYPE: PRT
<213> ORGANISM: Human

<400> SEQUENCE: 61

Arg Tyr Leu Lys Asp Gln Gln Leu Leu Gly Ile Trp Gly Cys Ser Gly
  1               5                   10                  15

Lys Leu Ile Cys Thr Thr Ala Val Pro Trp Asn Ala Ser Trp Ser
            20                  25                  30

<210> SEQ ID NO 62
<211> LENGTH: 36
<212> TYPE: PRT
<213> ORGANISM: Human

<400> SEQUENCE: 62

Trp Asn Asn Met Thr Trp Met Glu Trp Asp Arg Glu Ile Asn Asn Tyr
  1               5                   10                  15

Thr Ser Leu Ile His Ser Leu Ile Glu Glu Ser Gln Asn Gln Gln Glu
            20                  25                  30

Lys Asn Glu Gln
        35

<210> SEQ ID NO 63
<211> LENGTH: 21
<212> TYPE: PRT
<213> ORGANISM: Human

<400> SEQUENCE: 63

Thr Lys Lys Thr Gln Leu Gln Leu Glu His Leu Leu Leu Asp Leu Gln
  1               5                   10                  15
```

```
Met Ile Leu Asn Gly
            20

<210> SEQ ID NO 64
<211> LENGTH: 25
<212> TYPE: PRT
<213> ORGANISM: Human

<400> SEQUENCE: 64

Leu Asn Gly Ile Asn Asn Tyr Lys Asn Pro Lys Leu Thr Arg Met Leu
 1               5                  10                  15

Thr Phe Lys Phe Tyr Met Pro Lys Lys
            20                  25

<210> SEQ ID NO 65
<211> LENGTH: 23
<212> TYPE: PRT
<213> ORGANISM: Human

<400> SEQUENCE: 65

His Leu Arg Pro Arg Asp Leu Ile Ser Asn Ile Asn Val Ile Val Leu
 1               5                  10                  15

Glu Leu Lys Gly Ser Glu Thr
            20

<210> SEQ ID NO 66
<211> LENGTH: 23
<212> TYPE: PRT
<213> ORGANISM: Human

<400> SEQUENCE: 66

Thr Ala Thr Ile Val Glu Phe Leu Asn Arg Trp Ile Thr Phe Cys Gln
 1               5                  10                  15

Ser Ile Ile Ser Thr Leu Thr
            20

<210> SEQ ID NO 67
<211> LENGTH: 30
<212> TYPE: PRT
<213> ORGANISM: Human

<400> SEQUENCE: 67

Gln Leu Thr Val Trp Gly Ile Lys Gln Leu Gln Ala Arg Ile Leu Ala
 1               5                  10                  15

Val Glu Arg Tyr Leu Lys Asp Gln Gln Leu Leu Gly Ile Trp
            20                  25                  30

<210> SEQ ID NO 68
<211> LENGTH: 21
<212> TYPE: PRT
<213> ORGANISM: Human

<400> SEQUENCE: 68

Thr Lys Lys Thr Gln Leu Gln Leu Glu His Leu Leu Leu Asp Leu Gln
 1               5                  10                  15

Met Ile Leu Asn Gly
            20

<210> SEQ ID NO 69
<211> LENGTH: 23
<212> TYPE: PRT
<213> ORGANISM: Human
```

-continued

```
<400> SEQUENCE: 69

Gln Gln Gln Asn Asn Leu Leu Arg Ala Ile Glu Ala Gln Gln His Leu
  1               5                  10                  15

Leu Gln Leu Thr Val Trp Gly
            20

<210> SEQ ID NO 70
<211> LENGTH: 23
<212> TYPE: PRT
<213> ORGANISM: Human

<400> SEQUENCE: 70

Gln Gln Gln Asn Asn Leu Leu Ala Ala Ile Glu Ala Gln Gln His Leu
  1               5                  10                  15

Leu Gln Leu Thr Val Trp Gly
            20

<210> SEQ ID NO 71
<211> LENGTH: 23
<212> TYPE: PRT
<213> ORGANISM: Human

<400> SEQUENCE: 71

Gln Gln Gln Asn Asn Leu Leu Arg Ala Ile Glu Arg Gln Gln His Leu
  1               5                  10                  15

Leu Gln Leu Thr Val Trp Gly
            20

<210> SEQ ID NO 72
<211> LENGTH: 23
<212> TYPE: PRT
<213> ORGANISM: Human

<400> SEQUENCE: 72

Gln Gln Gln Asn Asn Leu Leu Ala Ala Ile Glu Arg Gln Gln His Leu
  1               5                  10                  15

Leu Gln Leu Thr Val Trp Gly
            20

<210> SEQ ID NO 73
<211> LENGTH: 23
<212> TYPE: PRT
<213> ORGANISM: Human

<400> SEQUENCE: 73

Gln Gln Gln Asn Asn Leu Leu Arg Ala Ile Glu Ala Gln Gln Glu Leu
  1               5                  10                  15

Leu Gln Leu Thr Val Trp Gly
            20

<210> SEQ ID NO 74
<211> LENGTH: 23
<212> TYPE: PRT
<213> ORGANISM: Human

<400> SEQUENCE: 74

Gln Gln Gln Asn Asn Leu Leu Arg Ala Ile Glu Ala Gln Gln Gln Leu
  1               5                  10                  15

Leu Gln Leu Thr Val Trp Gly
            20
```

```
<210> SEQ ID NO 75
<211> LENGTH: 23
<212> TYPE: PRT
<213> ORGANISM: Human

<400> SEQUENCE: 75

Gln Gln Gln Asn Asn Leu Leu Arg Ala Ile Glu Ala Gln Gln His Leu
  1               5                  10                  15

Leu Arg Leu Thr Val Trp Gly
             20

<210> SEQ ID NO 76
<211> LENGTH: 23
<212> TYPE: PRT
<213> ORGANISM: Human

<400> SEQUENCE: 76

Gln Gln Gln Asn Asn Leu Leu Arg Ala Ile Glu Ala Gln Gln His Leu
  1               5                  10                  15

Leu Lys Leu Thr Val Trp Gly
             20

<210> SEQ ID NO 77
<211> LENGTH: 23
<212> TYPE: PRT
<213> ORGANISM: Human

<400> SEQUENCE: 77

Gln Gln Gln Asn Asn Leu Leu Arg Ala Ile Glu Ala Gln Gln Gln Leu
  1               5                  10                  15

Leu Lys Leu Thr Val Trp Gly
             20

<210> SEQ ID NO 78
<211> LENGTH: 30
<212> TYPE: PRT
<213> ORGANISM: Human

<400> SEQUENCE: 78

Gln Leu Thr Val Trp Gly Ile Lys Gln Leu Gln Ala Arg Ile Leu Ala
  1               5                  10                  15

Val Glu Arg Tyr Leu Lys Asp Gln Gln Leu Leu Gly Ile Trp
             20                  25                  30

<210> SEQ ID NO 79
<211> LENGTH: 30
<212> TYPE: PRT
<213> ORGANISM: Human

<400> SEQUENCE: 79

Gln Leu Thr Val Trp Gly Ile Lys Gln Leu Gln Ala Arg Ile Leu Ala
  1               5                  10                  15

Val Glu Arg Tyr Leu Lys Ala Gln Gln Leu Leu Gly Ile Trp
             20                  25                  30

<210> SEQ ID NO 80
<211> LENGTH: 30
<212> TYPE: PRT
<213> ORGANISM: Human

<400> SEQUENCE: 80

Gln Leu Thr Val Trp Gly Ile Lys Gln Leu Gln Ala Arg Ile Leu Ala
  1               5                  10                  15
```

Val Glu Ala Tyr Leu Lys Asp Gln Gln Leu Leu Gly Ile Trp
                20                  25                  30

<210> SEQ ID NO 81
<211> LENGTH: 30
<212> TYPE: PRT
<213> ORGANISM: Human

<400> SEQUENCE: 81

Gln Leu Thr Val Trp Gly Ile Lys Gln Leu Gln Ala Arg Ile Leu Ala
1               5                   10                  15

Val Glu Ala Tyr Leu Lys Ala Gln Gln Leu Leu Gly Ile Trp
                20                  25                  30

<210> SEQ ID NO 82
<211> LENGTH: 30
<212> TYPE: PRT
<213> ORGANISM: Human

<400> SEQUENCE: 82

Gln Leu Thr Val Trp Gly Ile Lys Gln Leu Gln Ala Arg Ile Leu Ala
1               5                   10                  15

Val Glu Asp Tyr Leu Lys Arg Gln Gln Leu Leu Gly Ile Trp
                20                  25                  30

<210> SEQ ID NO 83
<211> LENGTH: 30
<212> TYPE: PRT
<213> ORGANISM: Human

<400> SEQUENCE: 83

Gln Leu Thr Val Trp Gly Ile Lys Gln Leu Gln Ala Arg Ile Thr Ala
1               5                   10                  15

Val Glu Arg Tyr Leu Lys Asp Gln Gln Leu Leu Gly Ile Trp
                20                  25                  30

<210> SEQ ID NO 84
<211> LENGTH: 31
<212> TYPE: PRT
<213> ORGANISM: Human

<400> SEQUENCE: 84

Arg Tyr Leu Lys Asp Gln Gln Leu Leu Gly Ile Trp Gly Cys Ser Gly
1               5                   10                  15

Lys Leu Ile Cys Thr Thr Ala Val Pro Trp Asn Ala Ser Trp Ser
                20                  25                  30

<210> SEQ ID NO 85
<211> LENGTH: 31
<212> TYPE: PRT
<213> ORGANISM: Human

<400> SEQUENCE: 85

Lys Tyr Leu Lys Asp Gln Gln Leu Leu Gly Ile Trp Gly Cys Ser Gly
1               5                   10                  15

Lys Leu Ile Cys Thr Thr Ala Val Pro Trp Asn Ala Ser Trp Ser
                20                  25                  30

<210> SEQ ID NO 86
<211> LENGTH: 31
<212> TYPE: PRT
<213> ORGANISM: Human

```
<400> SEQUENCE: 86

Arg Tyr Leu Lys Asp Gln Ala Leu Leu Gly Ile Trp Gly Cys Ser Gly
 1               5                  10                  15

Lys Leu Ile Cys Thr Thr Ala Val Pro Trp Asn Ala Ser Trp Ser
            20                  25                  30

<210> SEQ ID NO 87
<211> LENGTH: 31
<212> TYPE: PRT
<213> ORGANISM: Human

<400> SEQUENCE: 87

Arg Tyr Leu Lys Asp Gln Gln Gln Leu Gly Ile Trp Gly Cys Ser Gly
 1               5                  10                  15

Lys Leu Ile Cys Thr Thr Ala Val Pro Trp Asn Ala Ser Trp Ser
            20                  25                  30

<210> SEQ ID NO 88
<211> LENGTH: 31
<212> TYPE: PRT
<213> ORGANISM: Human

<400> SEQUENCE: 88

Arg Tyr Leu Lys Asp Gln Ala Gln Leu Gly Ile Trp Gly Cys Ser Gly
 1               5                  10                  15

Lys Leu Ile Cys Thr Thr Ala Val Pro Trp Asn Ala Ser Trp Ser
            20                  25                  30

<210> SEQ ID NO 89
<211> LENGTH: 31
<212> TYPE: PRT
<213> ORGANISM: Human

<400> SEQUENCE: 89

Arg Tyr Leu Lys Asp Gln Ala Arg Leu Gly Ile Trp Gly Cys Ser Gly
 1               5                  10                  15

Lys Leu Ile Cys Thr Thr Ala Val Pro Trp Asn Ala Ser Trp Ser
            20                  25                  30

<210> SEQ ID NO 90
<211> LENGTH: 31
<212> TYPE: PRT
<213> ORGANISM: Human

<400> SEQUENCE: 90

Arg Tyr Leu Lys Asp Gln Gln Leu Leu Asn Ser Trp Gly Cys Ser Gly
 1               5                  10                  15

Lys Leu Ile Cys Thr Thr Ala Val Pro Trp Asn Ala Ser Trp Ser
            20                  25                  30

<210> SEQ ID NO 91
<211> LENGTH: 31
<212> TYPE: PRT
<213> ORGANISM: Human

<400> SEQUENCE: 91

Arg Tyr Leu Lys Asp Gln Gln Leu Leu Gly Ile Trp Gly Cys Ser Gln
 1               5                  10                  15

Lys Leu Ile Cys Thr Thr Ala Val Pro Trp Asn Ala Ser Trp Ser
            20                  25                  30
```

<210> SEQ ID NO 92
<211> LENGTH: 31
<212> TYPE: PRT
<213> ORGANISM: Human

<400> SEQUENCE: 92

Arg Tyr Leu Lys Asp Gln Gln Leu Leu Gly Ile Trp Gly Cys Ser Phe
 1               5                   10                  15

Lys Leu Ile Cys Thr Thr Ala Val Pro Trp Asn Ala Ser Trp Ser
            20                  25                  30

<210> SEQ ID NO 93
<211> LENGTH: 31
<212> TYPE: PRT
<213> ORGANISM: Human

<400> SEQUENCE: 93

Arg Tyr Leu Lys Asp Gln Gln Leu Leu Gly Ile Trp Gly Cys Ser Gly
 1               5                   10                  15

Lys Leu Ile Cys Thr Thr Ala Val Pro Trp Asn Ala Ser Ser Ser
            20                  25                  30

<210> SEQ ID NO 94
<211> LENGTH: 31
<212> TYPE: PRT
<213> ORGANISM: Human

<400> SEQUENCE: 94

Arg Tyr Leu Lys Asp Gln Gln Leu Leu Gly Ile Trp Gly Cys Ser Gly
 1               5                   10                  15

Lys Leu Ile Cys Thr Thr Ala Val Pro Trp Asn Ala Asp Thr Leu
            20                  25                  30

<210> SEQ ID NO 95
<211> LENGTH: 31
<212> TYPE: PRT
<213> ORGANISM: Human

<400> SEQUENCE: 95

Arg Tyr Leu Lys Asp Gln Gln Leu Leu Gly Ile Trp Gly Cys Ser Gly
 1               5                   10                  15

Lys Leu Ile Cys Thr Thr Ala Val Pro Trp Asn Ala Thr Asn Arg
            20                  25                  30

<210> SEQ ID NO 96
<211> LENGTH: 31
<212> TYPE: PRT
<213> ORGANISM: Human

<400> SEQUENCE: 96

Arg Tyr Leu Lys Asp Gln Gln Leu Leu Gly Ile Trp Gly Cys Ser Gly
 1               5                   10                  15

Lys Leu Ile Cys Thr Thr Ala Val Pro Trp Asn Ala Asn Thr Arg
            20                  25                  30

<210> SEQ ID NO 97
<211> LENGTH: 31
<212> TYPE: PRT
<213> ORGANISM: Human

<400> SEQUENCE: 97

Arg Tyr Leu Lys Asp Gln Gln Leu Leu Gly Ile Trp Gly Cys Ser Gly

-continued

```
                1               5                  10                 15
Lys Leu Ile Cys Thr Thr Ala Val Pro Trp Asn Ala Asn Thr Ser
                    20                  25                  30

<210> SEQ ID NO 98
<211> LENGTH: 36
<212> TYPE: PRT
<213> ORGANISM: Human

<400> SEQUENCE: 98

Trp Asn Asn Met Thr Trp Met Glu Trp Asp Arg Glu Ile Asn Asn Tyr
 1               5                  10                 15

Thr Ser Leu Ile His Ser Leu Ile Glu Glu Ser Gln Asn Gln Gln Glu
            20                  25                  30

Lys Asn Glu Gln
        35

<210> SEQ ID NO 99
<211> LENGTH: 36
<212> TYPE: PRT
<213> ORGANISM: Human

<400> SEQUENCE: 99

Trp Asn Asn Met Thr Trp Met Glu Trp Asp Arg Glu Ile Asn Asn Tyr
 1               5                  10                 15

Glu Ser Leu Ile His Ser Leu Ile Glu Glu Ser Gln Asn Gln Gln Glu
            20                  25                  30

Lys Asn Glu Gln
        35

<210> SEQ ID NO 100
<211> LENGTH: 36
<212> TYPE: PRT
<213> ORGANISM: Human

<400> SEQUENCE: 100

Trp Asn Asn Met Thr Trp Met Glu Trp Asp Arg Glu Ile Asn Asn Tyr
 1               5                  10                 15

Thr Ser Asn Ile His Ser Leu Ile Glu Glu Ser Gln Asn Gln Gln Glu
            20                  25                  30

Lys Asn Glu Gln
        35

<210> SEQ ID NO 101
<211> LENGTH: 23
<212> TYPE: PRT
<213> ORGANISM: Feline immunodeficiency virus

<400> SEQUENCE: 101

Glu Ala Ile Glu Lys Val Thr Gly Ala Leu Lys Ile Asn Asn Leu Arg
 1               5                  10                 15

Leu Val Thr Leu Glu His Gln
            20

<210> SEQ ID NO 102
<211> LENGTH: 23
<212> TYPE: PRT
<213> ORGANISM: Feline immunodeficiency virus

<400> SEQUENCE: 102

Glu Ala Ile Glu Lys Val Thr Arg Ala Leu Lys Ile Asn Asn Leu Arg
```

```
1               5                  10                 15
Leu Val Thr Leu Glu His Gln
            20

<210> SEQ ID NO 103
<211> LENGTH: 23
<212> TYPE: PRT
<213> ORGANISM: Feline immunodeficiency virus

<400> SEQUENCE: 103

Glu Ala Ile Glu Lys Val Thr Asp Ala Leu Lys Ile Asn Asn Leu Arg
 1               5                  10                 15

Leu Val Thr Leu Glu His Gln
            20

<210> SEQ ID NO 104
<211> LENGTH: 23
<212> TYPE: PRT
<213> ORGANISM: Feline immunodeficiency virus

<400> SEQUENCE: 104

Glu Ala Ile Glu Lys Val Thr Ala Ala Leu Lys Ile Asn Asn Leu Arg
 1               5                  10                 15

Leu Val Thr Leu Glu His Gln
            20

<210> SEQ ID NO 105
<211> LENGTH: 23
<212> TYPE: PRT
<213> ORGANISM: Feline immunodeficiency virus

<400> SEQUENCE: 105

Glu Ala Ile Glu Lys Val Thr Gln Ala Leu Lys Ile Asn Asn Leu Arg
 1               5                  10                 15

Leu Val Thr Leu Glu His Gln
            20

<210> SEQ ID NO 106
<211> LENGTH: 30
<212> TYPE: PRT
<213> ORGANISM: Feline immunodeficiency virus

<400> SEQUENCE: 106

Val Thr Leu Glu His Gln Val Leu Val Ile Gly Leu Lys Val Glu Ala
 1               5                  10                 15

Met Glu Lys Phe Leu Tyr Thr Ala Phe Ala Met Gln Glu Leu
            20                  25                 30

<210> SEQ ID NO 107
<211> LENGTH: 30
<212> TYPE: PRT
<213> ORGANISM: Feline immunodeficiency virus

<400> SEQUENCE: 107

Val Thr Leu Glu His Gln Val Leu Val Ile Gly Leu Lys Val Glu Ala
 1               5                  10                 15

Met Glu Ala Phe Leu Tyr Thr Ala Phe Ala Met Gln Glu Leu
            20                  25                 30

<210> SEQ ID NO 108
<211> LENGTH: 30
<212> TYPE: PRT
```

<213> ORGANISM: Feline immunodeficiency virus

<400> SEQUENCE: 108

Val Thr Leu Glu His Gln Val Leu Val Ile Gly Leu Lys Val Glu Ala
 1               5                  10                  15
Met Glu Asn Phe Leu Tyr Thr Ala Phe Ala Met Gln Glu Leu
            20                  25                  30

<210> SEQ ID NO 109
<211> LENGTH: 30
<212> TYPE: PRT
<213> ORGANISM: Feline immunodeficiency virus

<400> SEQUENCE: 109

Val Thr Leu Glu His Gln Val Leu Val Ile Gly Leu Lys Val Glu Ala
 1               5                  10                  15
Met Glu Tyr Phe Leu Tyr Thr Ala Phe Ala Met Gln Glu Leu
            20                  25                  30

<210> SEQ ID NO 110
<211> LENGTH: 30
<212> TYPE: PRT
<213> ORGANISM: Feline immunodeficiency virus

<400> SEQUENCE: 110

Val Thr Leu Glu His Gln Val Leu Val Ile Gly Leu Lys Val Glu Ala
 1               5                  10                  15
Met Glu Arg Phe Leu Tyr Thr Ala Phe Ala Met Gln Glu Leu
            20                  25                  30

<210> SEQ ID NO 111
<211> LENGTH: 30
<212> TYPE: PRT
<213> ORGANISM: Feline immunodeficiency virus

<400> SEQUENCE: 111

Val Thr Leu Glu His Gln Val Leu Val Ile Gly Leu Lys Val Glu Ala
 1               5                  10                  15
Met Glu Lys Phe Leu Lys Thr Ala Phe Ala Met Gln Glu Leu
            20                  25                  30

<210> SEQ ID NO 112
<211> LENGTH: 30
<212> TYPE: PRT
<213> ORGANISM: Feline immunodeficiency virus

<400> SEQUENCE: 112

Val Thr Leu Glu His Gln Val Leu Val Ile Gly Leu Lys Val Glu Ala
 1               5                  10                  15
Met Glu Lys Phe Leu Glu Thr Ala Phe Ala Met Gln Glu Leu
            20                  25                  30

<210> SEQ ID NO 113
<211> LENGTH: 30
<212> TYPE: PRT
<213> ORGANISM: Feline immunodeficiency virus

<400> SEQUENCE: 113

Val Thr Leu Glu His Gln Val Leu Val Ile Gly Leu Lys Val Glu Ala
 1               5                  10                  15
Met Glu Lys Phe Leu Gln Thr Ala Phe Ala Met Gln Glu Leu
            20                  25                  30

<210> SEQ ID NO 114
<211> LENGTH: 30
<212> TYPE: PRT
<213> ORGANISM: Feline immunodeficiency virus

<400> SEQUENCE: 114

Val Thr Leu Glu His Gln Val Leu Val Ile Gly Leu Lys Val Glu Ala
1               5                   10                  15

Met Glu Lys Phe Leu Arg Thr Ala Phe Ala Met Gln Glu Leu
            20                  25                  30

<210> SEQ ID NO 115
<211> LENGTH: 30
<212> TYPE: PRT
<213> ORGANISM: Feline immunodeficiency virus

<400> SEQUENCE: 115

Val Thr Leu Glu His Gln Val Leu Val Ile Gly Leu Lys Val Glu Ala
1               5                   10                  15

Met Glu Lys Phe Leu Ala Thr Ala Phe Ala Met Gln Glu Leu
            20                  25                  30

<210> SEQ ID NO 116
<211> LENGTH: 30
<212> TYPE: PRT
<213> ORGANISM: Feline immunodeficiency virus

<400> SEQUENCE: 116

Val Thr Leu Glu His Gln Val Leu Val Ile Gly Leu Lys Val Glu Ala
1               5                   10                  15

Met Glu Lys Phe Leu Tyr Thr Ala Phe Gln Met Gln Glu Leu
            20                  25                  30

<210> SEQ ID NO 117
<211> LENGTH: 30
<212> TYPE: PRT
<213> ORGANISM: Feline immunodeficiency virus

<400> SEQUENCE: 117

Val Thr Leu Glu His Gln Val Leu Val Ile Gly Leu Lys Val Glu Ala
1               5                   10                  15

Met Glu Lys Phe Leu Tyr Thr Ala Phe Lys Met Gln Glu Leu
            20                  25                  30

<210> SEQ ID NO 118
<211> LENGTH: 30
<212> TYPE: PRT
<213> ORGANISM: Feline immunodeficiency virus

<400> SEQUENCE: 118

Val Thr Leu Glu His Gln Val Leu Val Ile Gly Leu Lys Val Glu Ala
1               5                   10                  15

Met Glu Lys Phe Leu Tyr Thr Ala Phe Arg Met Gln Glu Leu
            20                  25                  30

<210> SEQ ID NO 119
<211> LENGTH: 30
<212> TYPE: PRT
<213> ORGANISM: Feline immunodeficiency virus

<400> SEQUENCE: 119

```
Val Thr Leu Glu His Gln Val Leu Val Ile Gly Leu Lys Val Glu Ala
  1               5                  10                 15

Met Glu Lys Phe Leu Tyr Thr Ala Phe Ala Met Gln Ile Leu
               20                  25                 30

<210> SEQ ID NO 120
<211> LENGTH: 30
<212> TYPE: PRT
<213> ORGANISM: Feline immunodeficiency virus

<400> SEQUENCE: 120

Val Thr Leu Glu His Gln Val Leu Val Ile Gly Leu Lys Val Glu Ala
  1               5                  10                 15

Met Glu Lys Phe Leu Tyr Thr Ala Phe Ala Met Gln Ala Leu
               20                  25                 30

<210> SEQ ID NO 121
<211> LENGTH: 30
<212> TYPE: PRT
<213> ORGANISM: Feline immunodeficiency virus

<400> SEQUENCE: 121

Val Thr Leu Glu His Gln Val Leu Val Ile Gly Leu Lys Val Glu Ala
  1               5                  10                 15

Met Glu Lys Phe Leu Tyr Thr Ala Phe Ala Met Gln Ser Leu
               20                  25                 30

<210> SEQ ID NO 122
<211> LENGTH: 30
<212> TYPE: PRT
<213> ORGANISM: Feline immunodeficiency virus

<400> SEQUENCE: 122

Val Thr Leu Glu His Gln Val Leu Val Ile Gly Leu Lys Val Glu Ala
  1               5                  10                 15

Met Glu Lys Phe Leu Tyr Thr Ala Phe Ala Met Gln Phe Leu
               20                  25                 30

<210> SEQ ID NO 123
<211> LENGTH: 33
<212> TYPE: PRT
<213> ORGANISM: Feline immunodeficiency virus

<400> SEQUENCE: 123

Lys Phe Leu Tyr Thr Ala Phe Ala Met Gln Glu Leu Gly Cys Asn Gln
  1               5                  10                 15

Asn Gln Phe Phe Cys Lys Ile Pro Leu Glu Leu Trp Thr Arg Tyr Asn
               20                  25                 30

Met

<210> SEQ ID NO 124
<211> LENGTH: 33
<212> TYPE: PRT
<213> ORGANISM: Feline immunodeficiency virus

<400> SEQUENCE: 124

Lys Phe Leu Tyr Thr Ala Phe Ala Met Gln Glu Leu Gly Cys Asn Gln
  1               5                  10                 15

Asn Lys Phe Phe Cys Lys Ile Pro Leu Glu Leu Trp Thr Arg Tyr Asn
               20                  25                 30

Met
```

```
<210> SEQ ID NO 125
<211> LENGTH: 33
<212> TYPE: PRT
<213> ORGANISM: Feline immunodeficiency virus

<400> SEQUENCE: 125

Lys Phe Leu Tyr Thr Ala Phe Ala Met Gln Glu Leu Gly Cys Asn Gln
 1               5                  10                  15

Asn Arg Phe Phe Cys Lys Ile Pro Leu Glu Leu Trp Thr Arg Tyr Asn
            20                  25                  30

Met

<210> SEQ ID NO 126
<211> LENGTH: 33
<212> TYPE: PRT
<213> ORGANISM: Feline immunodeficiency virus

<400> SEQUENCE: 126

Lys Phe Leu Tyr Thr Ala Phe Ala Met Gln Glu Leu Gly Cys Asn Gln
 1               5                  10                  15

Asn Gly Phe Phe Cys Lys Ile Pro Leu Glu Leu Trp Thr Arg Tyr Asn
            20                  25                  30

Met

<210> SEQ ID NO 127
<211> LENGTH: 33
<212> TYPE: PRT
<213> ORGANISM: Feline immunodeficiency virus

<400> SEQUENCE: 127

Lys Phe Leu Tyr Thr Ala Phe Ala Met Gln Glu Leu Gly Cys Asn Gln
 1               5                  10                  15

Asn Ala Phe Phe Cys Lys Ile Pro Leu Glu Leu Trp Thr Arg Tyr Asn
            20                  25                  30

Met

<210> SEQ ID NO 128
<211> LENGTH: 33
<212> TYPE: PRT
<213> ORGANISM: Feline immunodeficiency virus

<400> SEQUENCE: 128

Lys Phe Leu Tyr Thr Ala Phe Ala Met Gln Glu Leu Gly Cys Asn Gln
 1               5                  10                  15

Asn Gln Leu Phe Cys Lys Ile Pro Leu Glu Leu Trp Thr Arg Tyr Asn
            20                  25                  30

Met

<210> SEQ ID NO 129
<211> LENGTH: 33
<212> TYPE: PRT
<213> ORGANISM: Feline immunodeficiency virus

<400> SEQUENCE: 129

Lys Phe Leu Tyr Thr Ala Phe Ala Met Gln Glu Leu Gly Cys Asn Gln
 1               5                  10                  15

Asn Gln His Phe Cys Lys Ile Pro Leu Glu Leu Trp Thr Arg Tyr Asn
            20                  25                  30
```

Met

<210> SEQ ID NO 130
<211> LENGTH: 33
<212> TYPE: PRT
<213> ORGANISM: Feline immunodeficiency virus

<400> SEQUENCE: 130

Lys Phe Leu Tyr Thr Ala Phe Ala Met Gln Glu Leu Gly Cys Asn Gln
 1               5                  10                  15

Asn Gln Ile Phe Cys Lys Ile Pro Leu Glu Leu Trp Thr Arg Tyr Asn
            20                  25                  30

Met

<210> SEQ ID NO 131
<211> LENGTH: 33
<212> TYPE: PRT
<213> ORGANISM: Feline immunodeficiency virus

<400> SEQUENCE: 131

Lys Phe Leu Tyr Thr Ala Phe Ala Met Gln Glu Leu Gly Cys Asn Gln
 1               5                  10                  15

Asn Gln Ala Phe Cys Lys Ile Pro Leu Glu Leu Trp Thr Arg Tyr Asn
            20                  25                  30

Met

<210> SEQ ID NO 132
<211> LENGTH: 33
<212> TYPE: PRT
<213> ORGANISM: Feline immunodeficiency virus

<400> SEQUENCE: 132

Lys Phe Leu Tyr Thr Ala Phe Ala Met Gln Glu Leu Gly Cys Asn Gln
 1               5                  10                  15

Asn Gln Gln Phe Cys Lys Ile Pro Leu Glu Leu Trp Thr Arg Tyr Asn
            20                  25                  30

Met

<210> SEQ ID NO 133
<211> LENGTH: 33
<212> TYPE: PRT
<213> ORGANISM: Feline immunodeficiency virus

<400> SEQUENCE: 133

Lys Phe Leu Tyr Thr Ala Phe Ala Met Gln Glu Leu Gly Cys Asn Gln
 1               5                  10                  15

Asn Gln Arg Phe Cys Lys Ile Pro Leu Glu Leu Trp Thr Arg Tyr Asn
            20                  25                  30

Met

<210> SEQ ID NO 134
<211> LENGTH: 38
<212> TYPE: PRT
<213> ORGANISM: Feline immunodeficiency virus

<400> SEQUENCE: 134

Trp Asn His Gly Asn Ile Thr Leu Gly Glu Trp Tyr Asn Gln Thr Lys
 1               5                  10                  15

Asp Leu Gln Gln Lys Phe Tyr Glu Ile Ile Met Asp Ile Glu Gln Asn
            20                  25                  30

-continued

Asn Val Gln Gly Lys Thr
            35

<210> SEQ ID NO 135
<211> LENGTH: 38
<212> TYPE: PRT
<213> ORGANISM: Feline immunodeficiency virus

<400> SEQUENCE: 135

Trp Asn His Gly Asn Ile Thr Leu Gly Glu Trp Tyr Asn Gln Thr Lys
 1               5                  10                  15

Asp Leu Gln Asn Lys Phe Tyr Glu Ile Ile Met Asp Ile Glu Gln Asn
            20                  25                  30

Asn Val Gln Gly Lys Thr
            35

<210> SEQ ID NO 136
<211> LENGTH: 38
<212> TYPE: PRT
<213> ORGANISM: Feline immunodeficiency virus

<400> SEQUENCE: 136

Trp Asn His Gly Asn Ile Thr Leu Gly Glu Trp Tyr Asn Gln Thr Lys
 1               5                  10                  15

Asp Leu Gln His Lys Phe Tyr Glu Ile Ile Met Asp Ile Glu Gln Asn
            20                  25                  30

Asn Val Gln Gly Lys Thr
            35

<210> SEQ ID NO 137
<211> LENGTH: 38
<212> TYPE: PRT
<213> ORGANISM: Feline immunodeficiency virus

<400> SEQUENCE: 137

Trp Asn His Gly Asn Ile Thr Leu Gly Glu Trp Tyr Asn Gln Thr Lys
 1               5                  10                  15

Asp Leu Gln Ser Lys Phe Tyr Glu Ile Ile Met Asp Ile Glu Gln Asn
            20                  25                  30

Asn Val Gln Gly Lys Thr
            35

<210> SEQ ID NO 138
<211> LENGTH: 38
<212> TYPE: PRT
<213> ORGANISM: Feline immunodeficiency virus

<400> SEQUENCE: 138

Trp Asn His Gly Asn Ile Thr Leu Gly Glu Trp Tyr Asn Gln Thr Lys
 1               5                  10                  15

Asp Leu Gln Ala Lys Phe Tyr Glu Ile Ile Met Asp Ile Glu Gln Asn
            20                  25                  30

Asn Val Gln Gly Lys Thr
            35

<210> SEQ ID NO 139
<211> LENGTH: 38
<212> TYPE: PRT
<213> ORGANISM: Feline immunodeficiency virus

<400> SEQUENCE: 139

```
Trp Asn His Gly Asn Ile Thr Leu Gly Glu Trp Tyr Asn Gln Thr Lys
  1               5                  10                  15

Asp Leu Gln Gly Lys Phe Tyr Glu Ile Ile Met Asp Ile Glu Gln Asn
             20                  25                  30

Asn Val Gln Gly Lys Thr
         35
```

<210> SEQ ID NO 140
<211> LENGTH: 38
<212> TYPE: PRT
<213> ORGANISM: Feline immunodeficiency virus

<400> SEQUENCE: 140

```
Trp Asn His Gly Asn Ile Thr Leu Gly Glu Trp Tyr Asn Gln Thr Lys
  1               5                  10                  15

Asp Leu Gln Glu Lys Phe Tyr Glu Ile Ile Met Asp Ile Glu Gln Asn
             20                  25                  30

Asn Val Gln Gly Lys Thr
         35
```

<210> SEQ ID NO 141
<211> LENGTH: 14
<212> TYPE: PRT
<213> ORGANISM: Human

<400> SEQUENCE: 141

```
Lys Thr Gln Leu Gln Leu Glu His Leu Leu Leu Thr Leu Gln
  1               5                  10
```

<210> SEQ ID NO 142
<211> LENGTH: 17
<212> TYPE: PRT
<213> ORGANISM: Human

<400> SEQUENCE: 142

```
Arg Pro Arg Asp Leu Ile Ser Asn Ile Asn Val Ile Val Leu Glu Leu
  1               5                  10                  15

Lys
```

<210> SEQ ID NO 143
<211> LENGTH: 21
<212> TYPE: PRT
<213> ORGANISM: Human

<400> SEQUENCE: 143

```
Thr Ile Val Glu Phe Leu Asn Arg Trp Ile Thr Phe Cys Gln Ser Ile
  1               5                  10                  15

Ile Ser Thr Leu Thr
             20
```

<210> SEQ ID NO 144
<211> LENGTH: 21
<212> TYPE: PRT
<213> ORGANISM: Human

-continued

```
<400> SEQUENCE: 144

Asn Asn Tyr Lys Asn Pro Lys Leu Thr Arg Met Leu Thr Phe Lys Phe
  1               5                  10                 15

Tyr Met Pro Lys Lys
             20
```

POLYNUCLEOTIDE ENCODING A MUTATED HIV GP41 POLYPEPTIDE

This is a Division of application Ser. No. 09/570,921 filed May 15, 2000, now U.S. Pat. No. 6,455,265, which in turn is a Continuation of application Ser. No. PCT/FR98/02447 filed Nov. 17, 1998.

The present invention relates to a method for obtaining vaccines for preventing the pathogenic effects related, in humans and in vertebrate animals, to retroviral infections.

The pathogenic effects related to a retroviral infection are the harmful effects, including possible oncogenic or immunosuppressive effects, induced by the introduction of a retrovirus into the body of a host (mammal, bird or alternatively fish), followed by the penetration and by the replication of said retrovirus in the cells of the host which are target cells for the retrovirus, that is to say cells into which the virus is capable of penetrating.

Retroviruses are thus named because they have the capacity, by virtue of the enzyme called reverse transcriptase, of carrying out transcription of RNA to DNA, whereas in living beings, the genetic information usually goes from the DNA of the chromosomes to proteins, via messenger RNA.

Three subfamilies can be distinguished in the retroviral family: the oncoviruses, the lentiviruses and the spumaviruses.

The oncoviruses are retroviruses thus termed because they can be associated with cancers and malignant infections. There may be mentioned, for example, leukemogenic viruses (such as the avian leukemia virus (ALV), the murine leukemia virus (MULV), also called Moloney virus, the feline leukemia virus (FELV), human leukemia viruses such as HTLV1 and HTLV2, the simian leukemia virus or STLV, the bovine leukemia virus or BLV), the primate type D oncoviruses, the type B oncoviruses which are inducers of mammary tumors, or oncoviruses which cause a rapid cancer (such as the Rous sarcoma virus or RSV); see for example STEHELIN et al., J. Mol. Biol. 101: 349-365 (1976).

The lentiviruses are thus named because they are responsible for slow-progressing pathological conditions which very frequently involve immunosuppressive phenomena, including AIDS.

The appended Table 1 indicates, by way of illustration, the pathological conditions associated with some lentiviruses, as well as the main target cells for these lentiviruses.

The spumaviruses manifest fairly low specificity for a given cell type or a given species, and they are sometimes associated with immunosuppressive phenomena; that is the case, for example, for the simian foamy virus (or SFV).

One of the aims of the present invention is the development of methods and vaccine products intended for effectively preventing the pathogenic effects, including the oncogenic or immunosuppressive effects, related to the infection of a host organism by a retrovirus.

Immunosuppression related to infection has been observed for a large number of retroviruses, and may be considered as a pathogenic constant of retroviral infection; see in particular BENDINELLI et al., Advances in Cancer Research 45: 125-181 (1985). This is the case in particular for lentivirus infections. It is also the case in a good number of oncovirus infections; see for example P. SONIGO in the book "SIDA et infection par VIH" [AIDS and HIV Infection], MONTAGNIER et al. (Médecine Science Flammarion), pages 113-122 (1989).

Many human and animal vaccines have been tested for preventing the pathogenic effects of retrovirus infections but, as a general rule, these vaccines are not very effective or are ineffective. In particular, in the field of human or animal AIDS, it is observed that, 14 years after the discovery of the HIV virus (BARRE-SINOUSSI et al., Science 220: 868-871, 1983), it has not yet been possible to find a vaccine which is able to effectively stop a post-vaccine HIV or SIV infection; see for example LINHART et al., AIDS Research and Human Retroviruses 13: 593-599 (1997); VOGT et al., Vaccine 13: 202-208 (1995); and LETVIN et al., J. Virol. 69: 4569-4571 (1995).

The majority of the vaccine preparations used comprise proteins of the retroviral envelope in various forms, for example inactivated viruses, envelope proteins such as the gp 120 and gp 160 proteins of HIV (see in particular GORSE, G. J., Vaccine 10: 383-388, 1992), virus cores with envelope proteins, or envelope proteins associated with various vectors (chimeric viruses, bacteria); see Levy J. A., Trans. Med. Rev. 2 : 265-271, 1988 and Microbiol. Rev. 57: 183-289, 1993, in particular page 247.

Other preparations use fragments of the retroviral envelope or immunodominant peptides derived from the envelope glycoproteins, these peptides being presented in various forms (lipopeptides, peptides bound to a supporting protein), so as to make them immunogenic; see in particular Eriksson et al., Vaccine, 11: 859-865 (1993).

The vaccine strategies conventionally described, for example in the field of human, simian or feline AIDS, recommend not modifying the conserved and immunodominant epitopes of the envelope proteins, which may appear to be completely logical. Indeed, on the one hand, these conserved epitopes are common to different viral strains, which is favorable to the production of a vaccine which has to induce an immune response directed against a majority of strains. On the other hand, these immunodominant epitopes are well recognized by the cellular or humoral immune system during the vaccinal and infectious process and, moreover, they frequently represent neutralization sites; see for example HO et al., J. Virol. 61: 2024-2028 (1987); JOHNSON et al., J. Exp. Med. 175: 961-971 (1992); SHAFFERMAN et al., P.N.A.S. U.S.A. 88: 7126-7130 (1991); and HAMMOND et al., J. Immunol. 146: 1470-1477 (1991).

The method of the invention consists, by contrast, in modifying the conserved and immunodominant epitopes of certain proteins of the viral envelope, in order to obtain an effective vaccine.

Indeed, the authors of the present invention have discovered that conserved and immunodominant regions of the retroviral envelope may be responsible for harmful autoimmune phenomena. By way of example, in the case of human AIDS, they have observed that certain conserved and immunodominant regions of the HIV envelope exhibit three-dimensional structural analogies and/or cross-reactions with certain regions of at least one protein of the human immune system, such that the administration, as a vaccine, of a viral protein containing said intact regions induces an immune response which is responsible for harmful autoimmune reactions leading to vaccine failure.

At the origin of the present invention, there is, on the one hand, the observation mentioned above that conserved and immunodominant regions of certain retroviruses, usually present in vaccine preparations, are, precisely, in a good number of cases, regions which cause harmful autoimmune reactions because they exhibit three-dimensional structural analogies and/or cross-reactions with certain proteins of the host for the virus. At the origin of the present invention, there is also, on the other hand, the observation that said proteins of the host use the same target cell, or the same target cells, as said retroviruses. All these observations carried out by the authors of the invention have led them to think that the retroviral envelope proteins and the host proteins which exhibit three-dimensional structural analogies and/or cross-reactions bind in many cases to the same target cells and possess, on these target cells, common membrane receptors.

It is said that a protein exhibits cross-reactivity with another protein when it is possible to obtain, by in vivo or in vitro immunization with the aid of one of said proteins, an immune response also directed against the other protein, for example when this immunization induces a (so-called B type) humoral response and makes it possible to obtain and to select at least one monoclonal antibody which is capable of recognizing the other protein, or when the same cellular immune response (that is to say of the T type) induced in vitro by one of the proteins recognizes the two proteins, according to the known tests for detecting a T-type immune response, such as for example the tests for cytotoxicity in vitro. It is known that the term "immunization" denotes the process of induction of an immune response following stimulation, by bringing immunocompetent cells of a host into contact in vivo or in vitro with an antigen, and that one of the aims of the administration of a vaccine agent is precisely to obtain such an immunization.

The subject of the invention is therefore a method of obtaining a vaccine against the pathogenic effects related to the infection of an animal or human host by a retrovirus capable of penetrating into a target cell of said host, said target cell possessing a membrane receptor for a protein of said host, method in which a vaccine agent based on a polypeptide comprising at least part of an envelope protein of a pathogenic strain of said retrovirus is prepared, and in which said polypeptide is prepared in a modified form, it being understood that:

said part of the envelope protein is chosen from those which comprise at least one fragment of an immunodominant region of said envelope protein, said fragment containing at least one amino acid which is a conserved amino acid of said immunodominant region and which is present in said pathogenic strain, said polypeptide, in the unmodified state, induces an immune response directed both against said immunodominant region and against the protein of the host, and said modified polypeptide is chosen from those which induce an immune response directed against said immunodominant region of the envelope protein and not against the protein of the host.

In the definition of the method of the invention which has just been given, the vaccine agent is said to be "based" on a modified polypeptide. This means that the vaccine agent comprises such a modified polypeptide, but this does not mean that the vaccine agent is necessarily of an exclusively polypeptide nature. In fact, in this vaccine agent, said polypeptide may be optionally bound to (in particular covalently) or associated, in a manner known per se, with any biocompatible molecule which may be chosen, for example from polymers, lipids, peptides (including lipopeptides, glycopeptides, proteins), nucleic acids, oligosaccharides and the like. Said biocompatible molecule may in particular serve as a support for the polypeptide immunogenic agent. It can also serve to modify the conformation of the polypeptide and, in the latter case, said molecule should be considered as a substituent modifying the amino acid residue to which it is attached, said substituent thus modifying, in the final analysis, the antigenicity of the polypeptide of which this amino acid residue is a part.

The method of the invention may comprise, at least in a preliminary research phase, a step consisting in selecting the polypeptides (unmodified) comprising at least part, as defined above, of the viral envelope protein of a pathogenic strain of the retrovirus. This protein part, which comprises at least one immunogenic fragment of an immunodominant region, is such that the polypeptide (unmodified) is capable of inducing an immune response directed both against the viral protein (more precisely against the fragment of the immunodominant region contained in said part) and against the protein of the host, and it is the existence of such an immune response, directed against the viral envelope protein and against the protein of the host, which defines, in the present application, the pathogenic character of a viral strain. It is thus possible to select the polypeptides (unmodified) comprising such a fragment.

A polypeptide fragment is said to be immunogenic if the immunization of a host, in vivo or in vitro, with said fragment, optionally bound to an appropriate support (such as a protein, a lipid or a polypeptide), makes it possible to obtain an immune response (of the B type and/or of the T type, directed against said polypeptide fragment).

In the present application, when reference is made to an immune response, without any other specific information, it is an immune response of a vertebrate, following immunization in vitro or in vivo.

The method of the invention may also comprise at least one step consisting in modifying, in the manner which will be indicated below, a polypeptide thus selected, and in choosing among the polypeptides those modified, at least one modified polypeptide which induces an immune response directed against the viral envelope protein and not against the protein of the host.

Thus, while the prior art taught, as noted above, not to modify the conserved and immunodominant epitopes of the retroviral envelope proteins, the aim of the method of the invention is, by contrast, to modify the antigenicity of such epitopes so as to obtain a differential immune response with respect to the viral envelope protein and to a protein of the host.

It is known that in order to modify the antigenicity of an immunogenic fragment of a polypeptide, it is possible to modify said polypeptide with the aid of a mutation affecting at least one amino acid. A definition will be given later of what "mutation" should be understood to mean here. The mutated amino acid may be present in the immunogenic fragment, or even in a region of the polypeptide outside said fragment. It is in fact known that the modification of an amino acid situated outside a fragment can affect the spatial structure of said fragment and therefore its antigenicity; in particular, it has been shown that the conformation of an amino acid residue, in a peptide, can be influenced by the nature of the amino acid residues at positions going from +8 to −8 relative to this amino acid residue; see for example GARNIER et al., J. Mol. Biol. 120: 97-120 (1978). Beyond this, the nature of the amino acid residues still has an influence, but this influence is neither symmetrical nor quantifiable from the sole knowledge of the peptide sequence considered.

A mutated amino acid can therefore be situated in the modified polypeptide, inside or outside the immunogenic fragment. When it is outside the immunogenic fragment, it is generally not separated from the nearest end of said immunogenic fragment, in the polypeptide chain, by more than eight (and in particular by more than seven) amino acid residues. In particular, an amino acid, mutated in accordance with the present invention, and situated outside the immunogenic fragment, is generally not separated by more than eight amino acid residues, and in particular by more than seven amino acid residues, from the nearest conserved amino acid belonging to the immunodominant region of which at least one fragment is contained in the unmodified polypeptide.

The modified polypeptide in accordance with the present invention may be, for example, the whole envelope protein of a pathogenic viral strain, modified by at least one mutation as indicated above. The modified polypeptide may also be part of the envelope protein of a pathogenic viral strain, modified by at least one mutation as indicated above, said part comprising at least one immunogenic fragment as defined above. The modified polypeptide may also be a chimeric protein comprising at least part of the envelope protein, said part of the envelope protein being as defined above and comprising at least one mutation.

The modified polypeptide used according to the invention may be, for example, a transmembrane glycoprotein of a retrovirus or a fragment of a transmembrane glycoprotein, in particular a fragment comprising an outer region of said transmembrane glycoprotein (modified), that is to say a region which is present on the outer surface of the viral membrane. Of course, such a protein fragment comprises at least part of an immunodominant region, as indicated above. When reference is made to an "outer" region of a protein, it is more precisely its surface which is accessible to the solvent, which may be defined in particular with the aid of software such as X-plor (see below) using the algorithm described by Lee & Richards, J. Mol. Biol. 55: 379-400, 1971. Said polypeptide may also be in the form of an oligomer of at least part of said transmembrane glycoprotein, in the modified state.

The definition given above of the method of the invention implies that the polypeptide used comprises at least part of an immunodominant and conserved region of a viral envelope protein. In the description of the present application, "conserved region" describes a region, optionally reduced to a single amino acid residue, of the viral protein, where, for a majority of strains of a given virus (for example in at least 6 strains out of 10 approximately), there are one or more identical or functionally analogous amino acids situated at the same position in peptide sequence alignments of said protein of the various strains. Such an identical or functionally analogous amino acid is called conserved amino acid. The notion of conservation of functionally analogous amino acids is known, and there are numerous substitution matrices which make it possible to quantify this notion (Dayhoff, M. O. et al., in Atlas of Protein Sequence and Structure, 1978, Vol. 5, Suppl. 3, Chapters 22 and 23).

The conserved regions can be easily determined, after sequencing of proteins of various strains of the virus studied, by methods of multiple alignments of the sequences obtained. For that, it is possible to use, for example, the Clustal-w program (Thompson J. D. et al., Nucleic Acids Research 22: 4673-4680, 1994). Moreover, the protein sequences of various viral strains are often accessible on data banks. For example, the Web server of the Los Alamos HIV data base has the HIV1, HIV2, SIV and FIV sequences which are regularly updated. The address of this server on the Internet network is:

http://hiv-web.lanl.gov/HTML/sequences.html

The appended Tables 2a, 2b, 2c and 2d are examples of sequence alignment of the regions belonging to the homologous envelope glycoproteins of region 545-682 of the HIV transmembrane glycoprotein (entry SWISSPROT ENV_HV1 BR), respectively for HIV1, HIV2, FIV and SIV. Table 2a shows the sequences represented by SEQ ID NOs: 1-29 in number order from top to bottom. Table 2b shows the sequences represented by SEQ ID NOs: 30-39 in number order from top to bottom. Table 2c shows the sequences represented by SEQ ID NOs: 40-46 in number order from top to bottom. Table 2d shows the sequences represented by SEQ ID NOs: 47-57 in number order from top to bottom. The last line of the tables summarizes, with the aid of symbols, the degree of homology and therefore the degree of conservation observed. The symbol "*" indicates a position of the alignment where the same residue is present in all the sequences, the symbol ":" indicates a position in the alignment where the amino acids present in the various sequences are very similar, the symbol "." indicates a position in the alignment where the amino acids present in the various sequences are similar, and the absence of a symbol indicates a position in the alignment where the amino acids present in the various sequences are not very similar. This symbolic system is used by the Clustal W alignment program (version 1.7).

The definition of the method of the invention makes reference to the target cells of a virus which are the cells into which the virus is capable of penetrating. The target cells of retroviruses are generally known. Viruses have the property of binding to the cells which they are capable of infecting. It is therefore optionally possible to test for, using routine experiments in vitro, the target cells of a virus studied.

The definition of the method of the invention also makes reference to the cells of the host having a membrane receptor for a protein of the host. The cells of the host which have a receptor for a protein of said host are often known and, in the opposite case, it is possible, using routine experiments, to determine if a given protein binds to a certain type of cell. It is possible, for example, to use a radiolabelled protein and to determine if it binds to said cell type. It is also possible to test if the protein binds to a given membrane receptor using a cell line transfected with a gene expressing said membrane receptor.

The proteins of the host for which certain cells of the host possess a membrane receptor are mainly proteins belonging to the range of soluble protein mediators. This range includes proteins called, depending on the cases, hormones, growth factors or cytokines, although there is no distinct boundary between these various categories of mediators; see for example CAVAILLON J. M., Les Cytokines (Masson, Paris, 1996) Chapter 1, pages 1-3 and preface.

In the present application, it is considered that an immune response, for example an antibody response, obtained by immunization with the aid of the modified polypeptide prepared in accordance with the method of the invention, is directed against the viral envelope protein and not against the protein of the host, when the antibodies obtained have affinities for the protein of the host and for the envelope protein of the retrovirus which exhibit a substantial difference, resulting in particular in differences in reactivity which are considered to be very significant in ELISA tests, such as for example optical densities in a ratio of about 4 (or more), which means that the optical density observed after attachment of said antibodies to the viral protein is at least four times higher than that observed for the attachment of said antibodies to the protein of the host. Similarly, a cellular type immune response is considered to be directed against the envelope protein but not against the protein of the host when the immunization in vitro of immunocompetent cells of the host with the candidate vaccine induces the formation of activated cells whose reaction toward cells (including transfected cell lines) expressing the retroviral envelope protein is significantly higher than the reaction toward cells expressing the protein of the host, for example when, in the final optical measurement, or in the final radioactivity counting (in particular $^{51}$Cr radioactivity released by target cells) of the test used, or alternatively in the assessment by any known means of a cell lysis caused by induced cytotoxic cells, the scales of response are in a ratio of about 4 (or more). The criteria which have just been indicated make it possible at least to make a first choice among the modified peptides studied, but in the final analysis, it is the absence or the decrease in the pathogenic effect due to the suppression or the weakening (demonstrated by any appropriate means) of the immune response toward the protein of the host which will constitute the criterion for selection of the modified peptides capable of constituting satisfactory vaccine agents.

The immunodominant and conserved regions of which it is desired to modify the antigenicity, in accordance with the invention, may be chosen from those which give in vitro a cross-reaction, of the B type and/or of the T type, with the host protein defined above.

It is also possible to choose such an immunodominant and conserved region from those for which a three-dimensional structural analogy with a region of said protein of the host has been determined beforehand, said structural analogy being capable of being associated with a cross-reaction in vitro and/or in vivo. The three-dimensional structural analogy between certain regions of two proteins refers to equivalent arrangements, in space, of amino acid residues which are similar because, in particular, of their side chain and/or of their analogous functional chemical groups. The three-dimensional structures of the proteins can be obtained with the aid of nuclear magnetic resonance (NMR) spectra and/or of X-ray diffraction spectra. For example, the structure of the SIV gp41 protein was obtained with the aid of the NMR spectrum (Caffrey M. et al., J. Mol. Biol. 271, 819-826, 1997). In addition, it is possible, in some cases, to obtain a good model with the aid of molecular modeling techniques, from the atomic coordinates of a protein of known structure. It is possible to use for that, in particular, the molecular modeling software X-plor (reference: "A system for X-ray crystallography and NMR, Version 3.1", Axel T. Brunger, Yale University Press, 1992).

To search for a three-dimensional structural analogy, it is possible to use, for example, the known methods of visualization and superposition on a graphic screen of the three-dimensional structure of biological molecules. Software exists which allows the visualization of the three-dimensional structures of the molecules with different modes of representation, the calculation of the geometric parameters (such as distances, angles and the like) and the objective and quantitative superposition of several molecular structures (in particular RASMOL software: Sayle, R. A. and Milner-White E. J., J. Mol. Biol., 247, 536-540, 1995 and ANTHEP-ROT software: Geourjon C. and Deléage G., J. Mol. Graph. 13, 209-212, 1995) as well as the estimation of the accessibility to solvents (X-plor software, already mentioned, and CCP4 software: Collaborative Computational Project Number 4, Acta Cryst., D50, 760-763, 1994.

However, in order to have a finer estimation of these structural analogies, it is useful to consider, at the level of each amino acid, the functional groups positioned in a similar manner in both proteins which are compared. For that, the co-inventors of the present invention use methods which make it possible to calculate molecular surface areas with the aim of comparing functional properties between two three-dimensional structures, in order to take into account, not amino acids in their entirety, but also, more particularly, functional chemical groups of each of them (for example: amide, carboxyl, hydroxyl, sulfhydryl and amine functions and the like). It is thus possible to take into consideration, in the structures compared, functionally analogous amino acids, and not only identical amino acids.

It is therefore considered that a region of a retroviral protein exhibits a three-dimensional structural analogy with a given region of a protein of the host when the techniques which have just been mentioned make it possible to demonstrate, in the two regions compared, a similar spatial organization of certain identical or functionally analogous amino acids.

It should be noted that amino acids which are functionally analogous and grouped together in a similar manner in space can be relatively distant from each other in the same peptide chain. However, the three-dimensional structural analogy between two proteins which are being compared can also relate to the spatial arrangement, in a similar manner, of identical or functionally analogous amino acids in the case where, one of the proteins being oligomerized, the amino acid residues involved are situated on different chains of the oligomer, whereas the amino acid residues of the other protein which are involved in this analogy can be situated on the same peptide chain of this other protein.

It is particularly advisable to search for three-dimensional structural analogies and/or cross-reactions with regions of the protein of the host which are involved in the attachment of said protein to its receptor.

Among the proteins of the host which are mentioned in the definition of the method of the invention, there may be mentioned in particular the soluble mediators as defined above. Taking into account the remark made above that immunosuppressive effects are generally associated with retroviral infections, it is particularly important to search for structural analogies and/or for cross-reactions between an outer protein of a retrovirus and soluble protein mediators of the immune system. Among these immune system mediators, there may be mentioned cytokines, and in particular interleukin-2, interleukin-10, interleukin-15 as well as interleukin-8 and chemokines.

To prepare the modified polypeptide which constitutes the vaccine agent obtained according to the invention, it is possible to use known methods of peptide synthesis or genetic engineering techniques. It is possible to isolate or to prepare a polynucleotide sequence encoding at least part of the envelope protein of the virus and, if desired, it is possible to introduce at this stage, into the nucleotide sequence, mutations which make it possible to obtain a mutated product of translation which constitutes the modified polypeptide. It is also possible to directly synthesize a modified polynucleotide sequence comprising one or more mutations and encoding the modified polypeptide. The mutated polynucleotide sequences thus obtained are introduced in a known manner into an appropriate vector which makes it possible to express said polypeptide, optionally in modified form. Such a vector is for example E. coli, a baculovirus or a mammalian cell. It is also possible to carry out the mutation on an unmodified polypeptide obtained according to one of the preceding methods.

In the present application, "mutation" refers to any modification of a region (optionally reduced to a single amino acid residue) of a polypeptide, by physical means, chemical means (covalent or noncovalent modification) and/or biological means (mutations by substitution, deletion and/or insertion of one or more amino acids), leading to the modification of the functional potentials of the constituent amino acid(s) of said region, termed "mutated region". By way of example, it is possible to carry out mutations leading to the abolition, acquisition and/or modulation of the properties of disulfide bridges, hydrogen bonds, electrostatic interactions and/or hydrophobic interactions, the modification of the capacity of a protein to form a heterocomplex, or alternatively, in the case of an oligomeric protein, the modification of the state of oligomerization or of the stability of the oligomer.

The modification of an amino acid a of a polypeptide chain (including the modification of a terminal amino acid of the polypeptide considered) can influence the conformation of the neighboring amino acids in the chain, including, as was recalled above, the conformation of an amino acid b separated from a by a number of amino acid residues which may be as high as seven or eight, and when the amino acid b is part of an epitope, any modification of the amino acid a (in particular any addition of a substituent or any modification of a substituent) is capable of modifying the antigenicity of the epitope considered.

In the phase for searching for modified polypeptides in accordance with the invention, the choice of the amino acids to be mutated and/or the choice of the mutation methods can be made in an arbitrary manner or in a reasoned manner. It is possible to use in particular at least one of the following methods of modification:

1) the replacement of one or more amino acids having a hydrophobic side chain (examples: Ala, Leu, Val, Ile, Phe, Trp, Met, Tyr, Cys) by one or more amino acids having a hydrophilic side chain (examples: Arg, Asp, Asn, Glu, Gln, Ser, Thr, His, Lys) or an indifferent chain (examples: Gly, Pro) and vice versa;
2) the replacement of one or more amino acids having a positively charged side chain (examples: Arg, Lys, His) by one or more amino acids having a negatively charged side chain (examples: Asp, Glu) or a neutral chain and vice versa;
3) the acquisition, suppression and/or modification of one or more disulfide bridges;
4) the production of mimotopes, in particular which are obtained by retro-inversion;
5) the substitutions, suppressions, additions and/or other modifications of at least one amino acid which is potentially a donor or acceptor of hydrogen bonds;
6) the substitutions, suppressions, additions and/or other modifications of at least one amino acid which is potentially a donor or acceptor of ionic bonds;
7) the change in steric hindrance by substitutions, suppressions, additions and/or other modifications of one or more amino acids;
8) the use of amino acids which are not naturally present in proteins;
9) the modification of glycosylation (creation, suppression or modification of glycosylation sites or of their associated sugars).

Of course, the modified polypeptides thus obtained are tested, as indicated above, in order to select the modified polypeptides which induce an immune response directed against the envelope protein and not against the protein of the host.

The method of the invention may be applied to the obtaining of vaccines, in particular against the following viruses: HIV, FIV, SIV, leukomogenic oncoviruses (avian, murine, feline, human, simian and bovine leukemia viruses, that is to say, respectively, ALV, MULV, FELV, HTLV, STLV, BLV), primate type D retroviruses, mammary tumor-inducing type B retroviruses, Rous sarcoma virus, maedi-visna virus (infecting sheep), feline sarcoma virus, avian myelocytomatosis virus and avian myeloblastosis virus.

The subject of the invention is also the use of a modified polypeptide, as defined above, in the preparation of a vaccine composition for preventing the pathogenic effects related to the infection of a host by a retrovirus.

The invention also relates to a vaccine composition which can be obtained by the method of the invention, and containing as active ingredient a modified polypeptide as described above. Such a composition may be used in a method of vaccination for preventing the pathogenic effects of retrovirus infections, this method essentially consisting in administering to a vertebrate animal, including a human, a modified polypeptide as defined above in a sufficient quantity to obtain a vaccination effect. The formulation of the vaccine compositions, and their method of administration, are known per se and will not be further described here.

The subject of the invention is also a modified retroviral polynucleotide encoding a modified polypeptide as defined above. The modified polynucleotide may be obtained as indicated above. The invention extends to an expression vector into which said modified polynucleotide has been inserted, said expression vector being thus capable of expressing the modified polypeptide.

The modified polypeptide obtained according to the invention can also serve as immunogenic agent in order to induce, by immunization, the formation of antibodies which can be used in particular in the treatment of retroviral infections, and the invention therefore also relates to the antibodies obtained in response to the immunization of animals (including humans), in vivo or in vitro, with the aid of the vaccine agent containing a modified polypeptide described above. The antibodies of the invention are in particular purified polyclonal antibodies or monoclonal antibodies exhibiting the characteristic of recognizing the retroviral envelope protein without recognizing the protein of the host. The purification of the polyclonal antibodies, and the selection of the monoclonal antibodies, can be carried out with the aid of the viral protein and of the protein of the host, so as to select only the antibodies which recognize the viral protein and not the protein of the host. The antibodies of the invention can be used in particular in the early treatment of infections caused in said host by the retrovirus against which they are directed. The dosage is the usual dosage for antibodies. The pharmaceutical compositions containing such antibodies also constitute one of the subjects of the invention.

The following examples illustrate the invention.

EXAMPLE 1

The manner in which the authors of the present invention searched for structural and antigenic analogies between an envelope protein of a virus, namely the gp41 protein of HIV1, and a cytokine, namely human interleukin-2 (abbreviated: IL-2), is presented below.

It will be noted that the peptide sequences of gp41 and of human IL-2 are not homologous. Indeed, the two proteins exhibit overall between them only 16.5% sequence identity, this threshold of homology not being significant, as can be easily noted with the aid of in silico simulations carried out on sequences having the same composition but in which the order of the amino acids has been randomly modified.

Previous studies (Bost et al., Immunology 65: 611-615, 1988) had reported a sequence homology between the protein gp41 and IL-2 (sequence LERILL). It should be noted that this LERILL sequence of gp41 does not constitute an immunodominant region of this protein; see LEVY J. A., Microbiol. Rev. 57: 183-289 (1993) in particular page 232. The sequence LERILL is in fact situated inside the viral particle; it corresponds to the C-terminal part of gp41.

Having observed that IL-2 and the AIDS-related retroviruses appear to have common target cells, the authors of the present invention made the hypothesis that the receptor for human interleukin-2 could be common to IL-2 and to the gp41 protein of HIV, and they therefore searched for possible three-dimensional structural analogies between the latter two.

In the present application, the numberings of the amino acid residues of the peptide sequence of interleukin-2 and of gp41 are those used in the SWISSPROT bank (version 34).

The peptide sequences of IL-2 and of the gp41 protein are known. In the present application, reference is made to the following published sequences:

for IL-2: SWISSPROT entry (version 34) which has the code IL2_HUMAN;

for gp41: SWISSPROT entry (version 34) which has the code ENV_HV1BR.

The published structures which have been used are the following:

for IL-2: PDB entry (Brookhaven Databank) 1IRL;

for gp41: PDB entries (Brookhaven Databank)
1AIK,
1ENV.

Moreover, the three-dimensional structure of IL-2, determined by NMR, is known (Mott, P. C. et al., J. Mol. Biol., 248: 979, 1995), as well as the structure of certain domains of the gp41 protein, which was obtained with the aid of the X-ray diffraction spectrum (Chan, D. C. et al., Cell, 89, 263-273, 1997; Weissenhorn, W. et al., Nature, 387, 426-430, 1997). Moreover, a three-dimensional model of part of the outer domain, in the 545-671 region, of the gp41 protein (trimeric form) was obtained, by molecular modeling, by the coinventors of the present invention. This molecular model was obtained using the X-plor software by a strategy similar to that of molecular modeling under NMR constraints. The constraints necessary for molecular modeling of the trimeric form were deduced from the three-dimensional structure of the pII mutant of the "leucine zipper" domain of the protein GCN4 (PDB code: 1GCM), crystallized in the form of a trimer of the "coiled coil" type.

By examining the structures obtained, three-dimensional analogies were found between certain regions of the gp41 protein and certain regions of interleukin-2 participating in the attachment to its receptor. The mode of attachment of IL-2 to its receptor, as well as the regions of IL-2 involved in this attachment, are indeed known; see BAZAN J. F., P.N.A.S. USA 87: 6934-6938 (1990); Bamborough P. et al., Structure 2: 839-851 (1994); Gnarra J., R. et al., P.N.A.S. USA 87: 3440-3444 (1990); Takeshita T. et al., Science 257: 379-382 (1992); and CAVAILLON J. M., Les Cytokines (Masson, Paris, 1996), pages 119-125.

These results have been confirmed by studies of overall comparison of the structures of gp41 and of IL-2, and also by local comparisons made by focusing more particularly on the analogous functional groups of each of the structures, as already indicated in the description above.

It was observed, in particular, that regions 53-61 and 88-93 of IL-2, organized in alpha-helix form, are superposed in a satisfactory manner with two of the three helices of the central trimer of gp41. This implies that in the two proteins, groups carried by different helices can have comparable properties of accessibility and relative organization.

Local three-dimensional structural analogies were also found between a highly conserved immunodominant region of the gp41 glycoprotein of HIV (more precisely in region 545-682 (SEQ ID NO: 58)) and human interleukin-2.

The peptide sequence of region 545-682 (SEQ ID NO: 58) of the gp41 protein of HIV1 (SWISSPROT code: ENV_HV1BR) is reproduced in the appended Table 3.

In the appended Table 3bis, the peptide sequences of four regions of this region of gp41 (555-577 (SEQ ID NO: 59), 572-601 (SEQ ID NO: 60), 590-620 (SEQ ID NO: 61) and 628-663 (SEQ ID NO: 62)) have been represented, in which structural analogies and/or cross-reactions were noted with IL-2.

The regions of IL-2 concerned by the structural analogies which have just been mentioned are the regions 27-47 (SEQ ID NO: 63), 45-69 (SEQ ID NO: 64), 99-121 (SEQ ID NO: 65) and 131-153 (SEQ ID NO: 66) of IL-2. The peptide sequences of these regions are represented in the appended Table 4.

It is important to note that region 27-47 (SEQ ID NO: 63) of IL-2 is involved in the attachment of IL-2 to the beta chain of its receptor. Indeed, the amino acids in region 2 7-47 belong to the A helix which participates in the attachment to the receptor for IL-2 (RIL-2), more precisely to beta RIL-2.

The amino acids in region 45-69 (SEQ ID NO: 64) belong to a region of IL-2 which participates in the attachment to alpha RIL-2.

The amino acids in region 99-121 (SEQ ID NO: 65) belong to the E helix participating in the attachment to beta RIL-2.

The amino acids in region 131-153 (SEQ ID NO: 66) of IL-2 belong to the F helix participating in the attatchment to gamma RIL-2.

By way of illustration, the structural analogies which were found between region 572-601 (SEQ ID NO: 60) of gp41 and region 27-47 (SEQ ID NO: 63) of human 11-2 are specified in the appended Table 4bis. The outer amino acids involved in this three-dimensional structural analogy are underlined in Table 4bis.

It should be noted, however, that the same region of gp41 can exhibit three-dimensional structural analogies with several distinct regions of IL-2.

In addition, the authors of the invention have observed that in region 600-612 of gp41, the three lysines (K) at position 606 on the three chains of gp41 trimer are capable of forming a conformational epitope, it being possible for these lysines of gp41 to correspond, in space, to lysines 52, 96 and 55 of IL-2.

They also observed immunological cross-reactivities between the IL-2 and gp41 proteins. In particular, using the ELISA and PEPSCAN techniques, with antibodies obtained from HIV+ sera purified by immunopurification on a column containing immobilized human IL-2, they observed that some of these antibodies recognize regions of LL-2 involved in the attachment of IL-2 to the alpha, beta and gamma chains of its receptor, and in particular regions belonging to the A helix (KTQLQLEHLLLTLQ) (SEQ ID NO: 141), the E helix (RPRDLISNINVIVLELK) (SEQ ID NO: 142), the F helix (TIVEFLNRWITFCQSIISTLT) (SEQ ID NO: 143), the AB loop and the beginning of the B helix (NNYKNP-KLTRMLTFKFYMPKK) (SEQ ID NO: 144).

Using the filter dot blot techniques and the Western blot-type immunotransfer techniques, it was also shown that the polyclonal antibodies obtained from sera of HIV+ patients, and immunopurified on human IL-2, recognize oligomers of the gp41 protein.

The studies carried out also showed that murine and human anti-gp41 monoclonal antibodies directed against immunodominant conserved regions of the gp41 protein of HIV recognize regions of IL-2 which participate in the attachment of the latter to the alpha, beta and gamma chains of the receptor for IL-2.

It is therefore possible to obtain vaccines against the HIV virus, in accordance with the invention, in particular by preparing polypeptides containing at least one of the regions of gp41 described in Table 3bis, the polypeptides being in modified form, that is to say containing at least one mutation, as indicated above. It should be clearly understood that these divisions of the region 545-682 (SEQ ID NO: 58) into regions can have a certain arbitrary character, and that is why some regions indicated may overlap.

EXAMPLE 2

Mutations on gp41 of HIV1

Mutated gp41 envelope glycoproteins are prepared according to known methods. These mutations are described in the appended Table 5 which represents the relevant sequence of gp41 and, aligned under the latter, the mutated sequences. Table 5 shows Region 555-577 (SEQ ID NO: 59) and Mutations 1-8, wherein the sequences of Mutations 1-8 are represented by SEQ ID NOs: 70-77 in number order from top to bottom. Table 5 also shows Region 572-601 (SEQ ID NO: 60) and Mutations 1-5, wherein the sequences of Mutations 1-5 are represented by SEQ ID NOs: 79-83 in number order from top to bottom. Table 5 also shows Region 590-620 (SEQ ID NO: 61) and Mutations 1-13, wherein the sequences of Mutations 1-13 are represented by SEQ ID NOs: 85-97 in number order from top to bottom. Table 5 also shows Region 628-663 (SEQ ID NO: 62) and Mutations 1-2, wherein the sequences of Mutations 1-2 are represented by SEQ ID NOs: 99-100 in number order from top to bottom. The level of the mutations is indicated by underlining the relevant amino acids.

Vaccine compositions are prepared each comprising, in sterile and pyrogen-free, aqueous saline solution, one of the mutated gp41 proteins obtained above.

Rabbits or mice are immunized with the mutated proteins obtained and it is determined whether the antibodies developed by these animals recognize or do not recognize human interleukin-2, for example by the ELISA or PEPSCAN technique. The mutated proteins which induce the formation of antibodies not recognizing IL-2, but recognizing the gp41 protein, are selected.

The PEPSCAN technique is described by J. WORTHINGTON and K. MORGAN, "Epitope mapping using synthetic peptides", in "PEPTIDE ANTIGENS-A practical approach" (G. B. WISDOW Ed.), Oxford University Press (1994).

EXAMPLE 3

Mutations on gp36 of FIV

The sequence of the gp36 protein of FIV is known (reference ENV_FIVPE).

Some of the sequences of this protein, homologous to the conserved regions of gp41 which are described in Table 3bis, have been represented in the appended Table 6, with examples of mutations. Table 6 shows various regions of the gp36 protein of FIV and mutations thereof, wherein the secinences are represented by SEQ ID NOs: 101-140 in number order from top to bottom.

TABLE 1

| LENTIVIRUS | HOST | PRINCIPAL TARGET CELL | |
| --- | --- | --- | --- |
| EIAV | Horse | Macrophage | Hemolytic anemia |
| VISNA VIRUS | Sheep | Macrophage | Maedi-visna: encephalitis-interstitial pneumonia |
| CAEV | Goat | Macrophage | Immunodeficiency-encephalopathy-arthritis |
| BIV | Bovine | T lymphocyte | Immunodeficiency-bovine lymphocytosis |
| FIV | Cats + Felidae | T lymphocyte | Immunodeficiency (AIDS) |
| SIV | Primates (monkeys) | T lymphocyte | Immunodeficiency (AIDS) |
| HIV | Humans | T lymphocyte | Immunodeficiency (AIDS) |

EIAV denotes the equine infectious anemia virus
CAEV denotes the caprine encephalitis virus
FIV means: feline immunodeficiency virus
SIV means: simian immunodeficiency virus
HIV means: human immunodeficiency virus

TABLE 2A

```
GP41_HV1Z2  QARQLLSGIVQQQNNLLRAIEAQQHLLQLTVWGIKQLQARILAVERYLKDQQLLGIWGCS

GP41_HV1Z6  QARQLMSGIVQQQNNLLRAIEAQQHLLQLTVWGIKQLQARILAVERYLKDQQLLGIWGCS

GP41_HV1EL  QARQLMSGIVQQQNNLLRAIEAQQHLLQLTVWGIKQLQARILAVERYLKDQQLLGIWGCS

GP41_HV1ND  QARQLMSGIVHQQNNLLRAIEAQQHLLQLTVWGIKQLQARVLAVERYLRDQQLLGIWGCS

GP41_HV1MA  QARQLLSGIVQQQNNLLRAIEAQQHLLQLTVWGIKQLQARVLAVERYLQDQRLLGMWGCS

GP41_HV1Z8  QARQLLSGIVQQQNNLLRAIEAQQHMLQLTVWGIKQLQARVLAVESYLKDQQLLGIWGCS

GP41_HV1C4  QARQLLSGIVQQQNNLLRAIKAQQHLLQLTVWGIKQLQARILAVERYLKDQQLLGFWGCS
```

TABLE 2A-continued

```
GP41_HV1S1  QARQLLSGIVQQQNNLLRAIEAQQHLLQLTVWGIKQLQARVLAVERYLKDQQLLGIWGCS
GP41_HV1BN  QARLLLSGIVQQQNNLLMAIEAQQHMLELTVWGIKQLQARVLAVERYLKDQQLLGIWGCS
GP41_HV1JR  QARQLLSGIVQQQNNLLRAIEAQQHMLQLTVWGIKQLQARVLAVERYLKDQQLMGIWGCS
GP41_HV1J3  QARLLLSGIVQQQNNLLRAIEGQQHLLQLTVWGIKQLQARILAVERYLKDQQLLGIWGCS
GP41_HV1SC  QARLLLSGIVQQQNNLLRAIEAQQHLLQLTVWGIKQLQARVLAVERYLRDQQLLGIWGCS
GP41_HV1KB  QARQLLPGIVQQQNNLLRAIDAQQHLLQLTVWGIKQLQARVLAVERYLKDQQLMGIWGCS
GP41_HV1Y2  QARQLLSGIVQQQNNLLRAIEAQQHLLQLTVWGIKQLQARVLAVERYLRDQQLLGIWGCS
GP41_HV1MN  QARLLLSGIVQQQNNLLRAIEAQQHMLQLTVWGIKQLQARVLAVERYLKDQQLLGFWGCS
GP41_HV1A2  QARQLLSGIVQQQNNLLRAIEAQQHLLQLTVWGIKQLQARVLAVERYLRDQQLLGIWGCS
GP41_HV1OY  QARQLLSGIVQQQNNLLRAIEAQQHLLQLTVWGIKQLQARVLAVERYLKDQQLLGIWGCS
GP41_HV1RH  QARHLLSGIVQQQNNLLRAIEAQQHLLQLTVWGIKQLQARVLAVERYLRDQQLLGIWGCS
GP41_HV1S3  QARKLLSGIVQQQNNLLRAIEAQQHLLQLTVWGIKQLQARVLAVERYLRDQQLLGIWGCS
GP41_HV1H2  QARQLLSGIVQQQNNLLRAIEAQQHLLQLTVWGIKQLQARILAVERYLKDQQLLGIWGCS
GP41_HV1H3  QARQLLSGIVQQQNNLLRAIEAQQHLLQLTVWGIKQLQARILAVERYLKDQQLLGIWGCS
GP41_HV1B1  QARQLLSGIVQQQNNLLRAIEAQQHLLQLTVWGIKQLQARILAVERYLKDQQLLGIWGCS
GP41_HV1PV  QARQLLSGIVQQQNNLLRAIEAQQHLLQLTVWGIKQLQARILAVERYLKDQQLLGIWGCS
GP41_HV1B8  QARQLLSGIVQQQNNLLRAIEGQQHLLQLTVWGIKQLQARILAVERYLKDQQLLGIWGCS
GP41_HV1MF  QARQLLSGIVQQQNNLLRAIEAQQHLLQLTVWGIKQLQARILAVERYLKDQQLLGIWGCS
GP41_HV1BR  QARQLLSGIVQQQNNLLRAIEAQQHLLQLTVWGIKQLQARILAVERYLKDQQLLGIWGCS
GP41_HV1W1  QARQLLSGIVQQQNNLLRAIEAQQHLLQLTVWGIKQLQARVLAVERYLRDQQLLGIWGCS
GP41_HV1W2  QARQLLSGIVQQQNNLLRAIDAQQHLLQLTVWGIKQLQARVLAVERYLRDQQLLGIWGCS
GP41_HV1ZH  QARRLLSGIVQQQNNLLRAIEAQQHLLKLTVWGIKQLQARILAVERYLKDQQLLGIWGCS
            *** *:.***:****** **..***:*:**********:**** **:**:*:*:****

GP41_HV1Z2  GKLICTTTVPWNSSWSNRSLNDIWQNMTWMEWEREIDNYTGLIYRLIEESQTQQEKNEQE
GP41_HV1Z6  GKLICTTTVPWNSSWSNRSLNDIWQNMTWMEWEREIDNYTGLIYRLIEESQTQQEKNEQE
GP41_HV1EL  GKHICTTNVPWNSSWSNRSLNEIWQNMTWMEWEREIDNYTGLIYSLIEESQTQQEKNEKE
GP41_HV1ND  GRHICTTNVPWNSSWSNRSLDEIWQNMTWMEWEREIDNYTGLIYSLIEESQIQQEKNEKE
GP41_HV1MA  GKHICTTFVPWNSSWSNRSLDDIWNNMTWMQWEKEISNYTGIIYNLIEESQIQQEKNEKE
GP41_HV1Z8  GKHICTTTVPWNSSWSNKSLEEIWNNMTWIEWEREIDNYTGVIYSLIENSQIQQEKNEQD
GP41_HV1C4  GKLICTTAVPWNASWSNKTLDQIWNNMTWMEWDREIDNYTHLIYTLIEESQNQQEKNQQE
GP41_HV1S1  GKLICTTAVPWNASWSNKSLDQIWNNMTWMEWEREIDNYTNLIYTLIEESQNQQEKNEQE
GP41_HV1BN  GKLICTTAVPWNASWSNKSLSDIWDNMTWMEWEREIDNYTNLIYSLIEDSQIQQEKNEKE
GP41_HV1JR  GKLICTTAVPWNTSWSNKSLDSIWNNMTWMEWEKEIENYTNTIYTLIEESQIQQEKNEQE
GP41_HV1J3  GKLICTTAVPWNASWSNKSLEEIWDNMTWMEWEREIDNYTSLIYTLIEESQNQQEKNEQE
GP41_HV1KB  GKFICTTAVPWNTSWSNKSFNEIWDNMTWMEWEREINNYTNLIYNLIEESQNQQEKNEQD
GP41_HV1Y2  GKLICTTTVPWNTSWSNKSLNEIWDNMTWMKWEREIDNYTHIIYSLIEQSQNQQEKNEQE
GP41_HV1MN  GKLICTTTVPWNASWSNKSLDDIWNNMTWMQWEREIDNYTSLIYSLLEKSQTQQEKNEQE
GP41_HV1A2  GKLICTTAVPWNASWSNKSLEDIWDNMTWMQWEREIDNYTNTIYTLLEESQNQQEKNEQE
GP41_HV1OY  GKLICTTTVPWNASWSNKSLNEIWDNMTWMQWEREIDNYTHLIYTLIEESQNQQEKNEQE
GP41_HV1RH  GKLICTTTVPWNASWSNKSLNMIWNNMTWMQWEREIDNYTGIIYNLLEESQNQQEKNEQE
```

TABLE 2A-continued

```
GP41_HV1S3  GKLICTTTVPWNTSWSNKSLDKIWNNMTWMEWEREIDNYTSLIYTLLEESQNQQEKNEQE

GP41_HV1H2  GKLICTTAVPWNASWSNKSLEQIWNHTTWMEWDREINNYTSLIHSLIEESQNQQEKNEQE

GP41_HV1H3  GKLLCTTAVPWNASWSNKSLEQIWNHTTWMEWDREINNYTSLIHSLIEESQNQQEKNEQE

GP41_HV1B1  GKLICTTAVPWNASWSNKSLEQIWNNMTWMEWDREINNYTSLIHSLIEESQNQQEKNEQE

GP41_HV1PV  GKLICTTAVPWNASWSNKSLEQIWNNMTWMEWDREINNYTSLIHSLIEESQNQQEKNEQE

GP41_HV1B8  GKLICTTAVPWNASWSNKSLEQIWNNMTWMEWDREINNYTSLIHSLIEESQNQQEKNEQE

GP41_HV1MF  GKLICTTAVPWNASWSNKSLEQFWNNMTWMEWDREINNYTSLIHSLIDESQNQQEKNEQE

GP41_HV1BR  GKLICTTAVPWNASWSNKSLEQIWNNMTWMEWDREINNYTSLIHSLIEESQNQQEKNEQE

GP41_HV1W1  GKLICTTTVPWNASWSNKSMDQIWNNMTWMEWEREIDNYTSLIYNLIEESQNQQEKNEQE

GP41_HV1W2  GKLICTTTVPWNASWSNKSMNQIWDNLTWMEWEREIDNYTSIIYSLIEESQNQQGKNEQE

GP41_HV1ZH  GKIICPTNVPWNSSWSNKSQSDIWDKMTWLEWDKEVSNYTQVIYNLIEESQTQQEINERD
            *:  :*  *  ****:****::  .  :*  *  **::*::*:.***   *:  *::.**  **   *:::

GP41_HV1Z2  LLELDKWASLWNWFNITQ

GP41_HV126  LLELDKWASLWNWFNITQ

GP41_HV1EL  LLELDKWASLWNWFSITQ

GP41_HV1ND  LLELDKWASLWNWFSITK

GP41_HV1MA  LLELDKWASLWNWFSISK

GP41_HV1Z8  LLQLDKWASLWNWFSITK

GP41_HV1C4  LLQLDKWASLWTWSDITK

GP41_HV1S1  LLELDKWASLWNWFDISK

GP41_HV1BN  LLELDKWASLWNWFNITN

GP41_HV1JR  LLELDKWASLWNWFGITK

GP41_HV1J3  LLGLDKWASLWNWFTTTN

GP41_HV1SC  LLELDKWASLWNWFNITN

GP41_HV1KB  LLALDKWDSLWNWFSITK

GP41_HV1Y2  LLALDKWASLWNWFDITK

GP41_HV1MN  LLELDKWASLWNWFDITN

GP41_HV1A2  LLELDKWASLWNWFSITN

GP41_HV1OY  LLELDKWAGLWSWFSITN

GP41_HV1RH  LLELDKWANLWNWFDITQ

GP41_HV1S3  LLELDKWASLWNWFSITN

GP41_HV1H2  LLELDKWASLWNWFNITN

GP41_HV1H3  LLELDKWASLWNWFNITN

GP41_HV1B1  LLELDKWASLWNWFNITN

GP41_HV1PV  LLELDKWANLWNWLNITN

GP41_HV1B8  LLELDKWASLWNWFNITN

GP41_HV1MF  LLELDKWASLWNWFNITN

GP41_HV1BR  LLELDKWASLWNWFNITN

GP41_HV1W1  LLELDKWASLWNWFSITN

GP41_HV1W2  LLELDKWASLWNWFDITN
```

TABLE 2A-continued

```
GP41_HV1ZH  LLALDKWANLWNWFDISN
            ** **** .**.*  *::
```

TABLE 2B

```
GP41_HV2D1  QSRTLLAGIVQQQQQLLDVVKRQQEMLRLTVWGTKNLQARVTAIEKYLKDQAQLNSWGCA

GP41_HV2G1  QSRTLLAGIVQQQQQLLDVVKRQQEMLRLTVWGTKNLQARVTAIEKYLKDQAQLNSWGCA

GP41_HV2BE  QSRTLLAGIVQQQQQLLDVVKRQQEMLRLTVWGTKNLQARVTAIEKYLKHQAQLNSWGCA

GP41_HV2NZ  QSRTLLAGIVQQQQQLLDVVKRQQEMLRLTVWGTKNLQARVTAIEKYLKDQAQLNSWGCA

GP41_HV2CA  QSRTLLAGIVQQQQQLLDVVKRQQELLRLTVWGTKILQARVTAIEKYLKDQAQLNSWGCA

GP41_HV2RO  QSRTLLAGIVQQQQQLLDVVKRQQELLRLTVWGTKNLQARVTAIEKYLQDQARLNSWGCA

GP41_HV2S2  QSRTSLAGIVQQQQQLLDVVKRQQEMLRLTVWGTKNLQARVTAIEKYLKDQAQLNSWGCA

GP41_HV2ST  QSRTLLAGIVQQQQQLLDVVKRQQEMLRLTVWGTKNLQARVTAIEKYLKDQAQLNSWGCA

GP41_HV2SB  QSRTLFRGIVQQQQQLLDVVKRQQEMLRLTVWGTKNLQARVTAIEKYLADQARLNSWGCA

GP41_HV2D2  QSRTLLAGIVQQQQQPVDVVKRQQELLRLTVWGTKNLQARVTAIEKYLKDQAQLNSWGCA
            **** : ******** :*********:********* ************ .**:*******

GP41_HV2D1  FRQVCHTTVPWVNDSLTPDWNNMTWQEWEKRVHYLEANISQSLEQAQIQQEKNMYELQKL

GP41_HV2G1  FRQVCHTTVPWVNDSLSPDWNNMTWQEWEKQVRYLEANISQSLEQAQIQQEKNMYELQKL

GP41_HV2BE  FRQVCHTTVPWVNDSLSPDWKNMTWQEWEKQVRYLEANISQSLEEAQIQQEKNMYELQKL

GP41_HV2N2  FRQVCHTSVPWVNDTLTPDWNNMTWQEWEQKVRYLEANISQSLEQAQIQQEKNMYELQKL

GP41_HV2CA  FRQVCHTTVPWANESLTPDWNNMTWQEWEQKVRYLEANISQSLEEAQLQQEKNMYELQKL

GP41_HV2RO  FRQVCHTTVPWVNDSLAPDWDNMTWQEWEKQVRYLEANISKSLEQAQIQQEKNMYELQKL

GP41_HV2S2  FRQVCHTTVPWVNDTLTPDWNNITWQEWEQRIRNLEANISESLEQAQIQQEKNMYELQKL

GP41_HV2ST  FRQVCHTTVPWVNDTLTPDWNNMTWQEWEQRIRNLEANISESLEQAQIQQEKNMYELQKL

GP41_HV2SB  FRQVCHTTVPWVNDTLTPEWNNMTWQEWEHKIRFLEANISESLEQAQIQQEKNMYELQKL

GP41_HV2D2  FRQVCHTTVPWPNETLTPNWNNMTWQQWEKQVHFLDANITALLEEAQIQQEKNMYELQKI
            ********:*** *::*:*:*.*:***:*:::: *:****  **:**:***********:

GP41_HV2D1  NSWDVFGNWFDLTS

GP41_HV2G1  NSWDVFGNWFDLTS

GP41_HV2BE  NSWDILGNWFDLTS

GP41_HV2NZ  NSWDVFTNWLDFTS

GP41_HV2CA  NNWDVFTNWFDLTS

GP41_HV2RO  NSWDIFGNWFDLTS

GP41_HV2S2  NSWDVFSNWFDLTS

GP41_HV2ST  NSWDVFGNWFDLTS

GP41_HV2SB  NSWDVFGNWFDLTS

GP41_HV2D2  NSWDVFGNWFDLTS
            *.**:: **:*:**
```

TABLE 2C

```
GP36_FIVPE  QYHQVLATHQEAIEKVTGALKINNLRLVTLEHQVLVIGLKVEAMEKFLYTAFAMQELGCN

GP36_FIVU1  QYHQVLATQQEAIEKVTEALKITNLRLVTLEHQVLVIGLKVEAMEKFLYTAFAMQELGCN
```

TABLE 2C-continued

```
GP36_FIVWO  QYQQVLATHQEAIEKVTEALKINNLRLVTLEHQVLVIGLKVEAMEKFLYTAFAMQELGCN

GP36_FIVU2  QYHQVLATHQETIEKITEALKVNNLRLVTLEHQVLVIGLKVEAIEKFLYTAFAMQELGCN

GP36_FIVU8  QYHQVLATHQETIEKVTEALKINNLRLVTLEHQVLVIGLKVEAMEKFLYTAFAMQELGCN

GP36_FIVSD  QYQQVLATHQEALDKITEALKINNLRLVTLEHQMLVIGLKVEAIEKFLYTAFAMQELGCN

GP36_FIVT2  QYHQVLATHQQALEKITEALKINNLRLITLEHQVLVIGLRVEAIEKFLYTAFAMQELGCN
            **:*****:*:::*:* ***:.****:*****:***:***:******************

GP36_FIVPE  QNQFFCKIPLELWTRYNMTINQTIWNHGNITLGEWYNQTKDLQQKFYEIIMDIEQNNVQG

GP36_FIVU1  QNQFFCKVPPELWRRYNMTINQTIWNHGNITLGEWYNQTKDLQKKFYGIIMDIEQNNVQG

GP36_FIVWO  QNQFFCKVPSALWERYNMTINQTIWNHGNITLGEWYNQTKDLQQRFYEIIMDIEQNNVQG

GP36_FIVU2  QNQFFCKVPPELWQRYNMTINQTIWNHGNITLGEWYNQTKDLQQKFYEIIMDMEQNNVQG

GP36_FIVU8  QNQFFCKVPPELWKRYNMTINQTIWNHGNITLGEWYNQTKELQQKFYEIIMNIEQNNVQV

GP36_FIVSD  QNQFFCEIPKELWLRYNMTLNQTIWNHGNITLGEWYNQTKYLQQKFYEIIMDIEQNNVQG

GP36_FIVT2  QNQFFCKIPPSLWSMYNMTLNQTIWNHGNISLGNWYNQTRDLQNKFYEIIMDIEQNNVQG
            ******::*  **  ****:***********:**:*****: **::** ***::******

GP36_FIVPE  KTGIQQLQKWEDWVRWIGNIPQ

GP36_FIVU1  KKGLQQLQKWEDWVGWIGNIPQ

GP36_FIVWO  KKGLQQLQEWEDWVGWIGNIPQ

GP36_FIVU2  RKGLQQLQEWEDWVGWLGNIPR

GP36_FIVU8  KKGLQQLQEWEDWVGWIGNIPQ

GP36_FIVSD  KQGLQKLQNWQDWMGWIGKIPQ

GP36_FIVT2  KTGIQQLQKWENWVGWIGKIPQ
             :*:*:**:*::*: *:*:**:
```

TABLE 2d

```
GP41_SIVMK  QSRTLLAGIVQQQQQLLGVVKRQQELLRLTVWGTKNLQTRVTAIEKYLEDQAQLNAWGCA

GP41_SIVML  QSRTLLAGIVQQQQQLLDVVKRQQELLRLTVWGTKNLQTKVTAIEKYLKDQAQLNAWGCA

GP41_SIVM1  QSRTLLAGIVQQQQQLLDVVKRQQELLRLTVWGTKNLQTRVSAIEKYLKDQAQLNAWGCA

GP41_SIVS4  QSRTLLAGIVQQQQQLLDVVKRQQELLRLTVWGTKNLQTRVTAIEKYLKDQAQLNSWGCA

GP41_SIVSP  QSRTLLAGIVQQQQQLLDVVKRQQELLRLTVWGAKNLQTRVTAIEKYLEDQAQLNSWGCA

G241_SIVAG  QSQHLLAGILQQQKNLLAAVEAQQQMLKLTIWGVKNLNARVTALEKYLEDQARLNAWGCA

GP41_SIVAT  QSRHLLAGILQQQKNLLAAVEAQQQMLKLTIWGVKNLNARVTALEKYLEDQARLNSWGCA

GP41_SIVA1  QSQHLLAGILQQQKNLLAAVGAQQQMLKLTIWGVKNLNARVTALEKYLADQARLNAWGCA

GP41_SIVAI  QSRHLLAGILQQQKNLLAAVEQQQQLLKLTIWGVKNLNARVTALEKYLEDQARLNSWGCA

GP41_SIVGB  QSQSLVTGIVEQQKQLLKLIEQQSELLKLTIWGVKNLQTRLTSLENYIKDQALLSQWGCS

GP41_SIVCZ  QARQLLSGIVQQQNNLLKAIEAQQHLLQLSIWGVKQLQARLLAVERYLQDQQILGLWGCS
            *::  *::**::****   :   *..:*:*::**.*:*::::  ::*.*: **  *. ***:

GP41_SIVMK  FRQVCHTTVPWPNASL-----TPDWNNDTWQEWERKVDFLEENITALLEEAQIQQEKNMY

GP41_SIVNL  FRQVCUITVPWPNASL-----TPDWNNDTWQEWERKVDFLEENITALLEEAQIQQEKNMY
```

TABLE 2d-continued

```
GP41_SIVM1  FRQVCHTTVPWPNASL-----TPDWNNETWQEWERKVDFLEANITALLEEAQIQQEKNMY

G241_SIVS4  FRQVCHTTVPWPNETL-----VPNWNNMTWQEWERQVDFLEANITQLLEEAQIQQEKNMY

GP41_SIVSP  FRQVCHTTVPRPNDTL-----TPNWNNMTWQEWEKQVNFLEANITQSLEEAQIQQEKNTY

GP41_SIVAG  WKQVCHTTVPWQWNNR-----TPDWNNMTWLEWERQISYLEGNITTQLEEARAQEEKNLD

GP41_SIVAT  WKQVCHTTVEWPWTNR-----TPDWQNMTWLEWERQIADLESNITGQLVKAREQEEKNLD

GP41_SIVA1  WKQVCHTTVPWTWNN------TPEWNNMTWLEWEKQIEGLEGNITKQLEQAREQEEKNLD

GP41_SIVAI  WKQVCHTTVPWKYNN------TPKWDNMTWLEWERQINALEGNITQLLEEAQNQESKNLD

GP41_SIVGB  WAQVCHTSVEWTNTSI-----TPNWTSETWKEWETRTDYLQQNITEMLKQAYDREQRNTY

GP41_SIVCZ  GKAVCYTTVPWNNSWPGSNSTDDIWGNLTWQQWDKLVSNYTGKIFGLLEEAQSQQEKNER
            **: :*               * . ** :*:      :*    * :*  ::..:*

GP41_SIVMK  ELQKLNSWDVFGNWFDLAS

GP41_SIVML  KLQKLNSWDVFGNWFDLAS

GP41_SIVN1  ELQKLNSWDVFGNWFDLTS

GP41_SIVS4  ELQKLNSWDIFGNWFDLTS

GP41_SIVSP  ELQKLNSWDIFGNWFDLTS

GP41_SIVAG  AYQKLSSWSDFWSWFDFSK

GP41_SIVAT  AYQKLTSWSDFWSWFDFSK

GP41_SIVA1  AYQKLSDWSSFWSWFDFSK

GP41_SIVAI  LYQKLDDWSGFWSWFSLST

GP41_SIVGB  ELQKLGDLTSWASWFDFTW

GP41_SIVCZ  DLLELDQWASLWNWFDITK
            :* . .**.::
```

TABLE 3 gp41 (region 545-682)

545 - QARQLLSGIVQQQNNLLRAIEAQQHLLQLTVWGIK

QLQARILAVERYLKDQQLLGIWGCSGKLICTTAVP

WNASWSNKSLEQIWNNMTWMEWDREINNYTSLIHS

LIEESQNQQEKNEQELLELDKWASLWNWFNITN - 682

TABLE 3bis

| Regions of gp41 | |
|---|---|
| Region 555-577 | QQQNNLLRAIEAQQHLLQLTVWG |
| Region 572-601 | QLTVWGIKQLQARILAVERYLKDQQLLGIW |
| Region 590-620 | RYLKDQQLLGIWGCSGKLICTTAVPWNASWS |
| Region 628-663 | WNNMTWMEWDREINNYTSLIHSLIEESQNQQEKNEQ |

TABLE 4

| IL-2 | |
|---|---|
| Region 27-47 | TKKTQLQLEHLLLDLQMILNG |
| Region 45-69 | LNGINNYKNPKLTRMLTFKFYMPKK |
| Region 99-121 | HLRPRDLISNINVIVLELKGSET |
| Region 131-153 | TATIVEFLNRWITFCQSIISTLT |

TABLE 4bis

| gp41 | IL-2 |
|---|---|
| Region 572-601 | Zone 27-47 |
| QLTVWGIKQLQARIL AVER YLKDQQLLGIW | TKKTQLQLEHLLLDLQMILNG |

TABLE 5

Mutations at the level of region 555-577

| | |
|---|---|
| Region 555-577 | QQQNNLLRAIEAQQHLLQLTVWG |
| Mutation 1: | QQQNNLLAAIEAQQHLLQLTVWG |
| Mutation 2: | QQQNNLLRAIERQQHLLQLTVWG |
| Mutation 3: | QQQNNLLAAIERQQHLLQLTVWG |
| Mutation 4: | QQQNNLLRAIEAQQELLQLTVWG |
| Mutation 5: | QQQNNLLRAIEAQQQLLQLTVWG |
| Mutation 6: | QQQNNLLRAIEAQQHLLRLTVWG |
| Mutation 7: | QQQNNLLRAIEAQQHLLKLTVWG |
| Mutation 8: | QQQNNLLRAIEAQQQLLKLTVWG |

Mutations at the level of region 572-601

| | |
|---|---|
| Region 572-601 | QLTVWGIKQLQARILAVERYLKDQQLLGIW |
| Mutation 1: | QLTVWGIKQLQARILAVERYLKAQQLLGIW |
| Mutation 2: | QLTVWGIKQLQARILAVEAYLKDQQLLGIW |
| Mutation 3: | QLTVWGIKQLQARILAVEAYLKAQQLLGIW |
| Mutation 4: | QLTVWGIKQLQARILAVEDYLKRQQLLGIW |
| Mutation 5: | QLTVWGIKQLQARITAVERYLKDQQLLGIW |

Mutations at the level of region 590-620

| | |
|---|---|
| Region 590-620 | RYLKDQQLLGIWGCSGKLICTTAVPWNASWS |

TABLE 5-continued

| | |
|---|---|
| Mutation 1: | KYLKDQQLLGIWGCSGKLICTTAVPWNASWS |
| Mutation 2: | RYLKDQALLGIWGCSGKLICTTAVPWNASWS |
| Mutation 3: | RYLKDQQQLGIWGCSGKLICTTAVPWNASWS |
| Mutation 4: | RYLKDQAQLGIWGCSGKLICTTAVPWNASWS |
| Mutation 5: | RYLKDQARLGIWGCSGKLICTTAVPWNASWS |
| Mutation 6: | RYLKDQQLLNSWGCSGKLICTTAVPWNASWS |
| Mutation 7: | RYLKDQQLLGIWGCSQKLICTTAVPWNASWS |
| Mutation 8: | RYLKDQQLLGIWGCSFKLICTTAVPWNASWS |
| Mutation 9: | RYLKDQQLLGIWGCSGKLICTTAVPWNASSS |
| Mutation 10: | RYLKDQQLLGIWGCSGKLICTTAVPWNADTL |
| Mutation 11: | RYLKDQQLLGIWGCSGKLICTTAVPWNATNR |
| Mutation 12: | RYLKDQQLLGIWGCSGKLICTTAVPWNANTR |
| Mutation 13: | RYLKDQQLLGIWGCSGKLICTTAVPWNANTS |

Mutations at the level of region 628-663

| | |
|---|---|
| Region 628-663 | WNNMTWMEWDREINNYTSLIHSLIEESQNQQEKNEQ |
| Mutation 1: | WNNMTWMEWDREINNYESLIHSLIEESQNQQEKNEQ |
| Mutation 2: | WNNMTWMEWDREINNYTSNIHSLIEESQNQQEKNEQ |

TABLE 6

| | |
|---|---|
| Region 651-673 | EAIEKVTGALKINNLRLVTLEHQ |
| Mutation 1 | EAIEKVT RALKINNLRLVTLEHQ |
| Mutation 2 | EAIEKVT DALKINNLRLVTLEHQ |
| Mutation 3 | EAIEKVT AALKINNLRLVTLEHQ |
| Mutation 4 | EAIEKVT QALKINNLRLVTLEHQ |
| Region 668-697 | VTLEHQVLVIGLKVEAMEKFLYTAFAMQEL |
| Mutation 1 | VTLEHQVLVIGLKVEAME AFLYTAFAMQEL |
| Mutation 2 | VTLEHQVLVIGLKVEAME YFLYTAFAMQEL |
| Mutation 3 | VTLEHQVLVIGLKVEAME NFLYTAFAMQEL |
| Mutation 4 | VTLEHQVLVIGLKVEAME RFLYTAFAMQEL |
| Mutation 5 | VTLEHQVLVIGLKVEAMEKFL KTAFAMQEL |
| Mutation 6 | VTLEHQVLVIGLKVEAMEKFL ETAFAMQEL |
| Mutation 7 | VTLEHQVLVIGLKVEAMEKFL QTAFAMQEL |
| Mutation 8 | VTLEHQVLVIGLKVEAMEKFL RTAFAMQEL |
| Mutation 9 | VTLEHQVLVIGLKVEAMEKFL ATAFAMQEL |
| Mutation 10 | VTLEHQVLVIGLKVEAMEKFLYTAF QMQEL |
| Mutation 11 | VTLEHQVLVIGLKVEAMEKFLYTAF KMQEL |
| Mutation 12 | VTLEHQVLVIGLKVEAMEKFLYTAF RMQEL |
| Mutation 13 | VTLEHQVLVIGLKVEAMEKFLYTAFAMQ IL |
| Mutation 14 | VTLEHQVLVIGLKVEAMEKFLYTAFAMQ AL |
| Mutation 15 | VTLEHQVLVIGLKVEAMEKFLYTAFAMQ SL |

TABLE 6-continued

| | |
|---|---|
| Mutation 16 | VTLEHQVLVIGLKVEAMEKFLYTAFAMQ FL |
| Region 686-718 | KFLYTAFAMQELGCNQNQFFCKIPLELWTRYNM |
| Mutation 1 | KFLYTAFAMQELGCNQN KFFCKIPLELWTRYNM |
| Mutation 2 | KFLYTAFAMQELGCNQN RFFCKIPLELWTRYNM |
| Mutation 3 | KFLYTAFAMQELGCNQN GFFCKIPLELWTRYNM |
| Mutation 4 | KFLYTAFAMQELGCNQN AFFCKIPLELWTRYNM |
| Mutation 5 | KFLYTAFAMQELGCNQNQ LFCKIPLELWTRYNM |
| Mutation 6 | KFLYTAFAMQELGCNQNQ HFCKIPLELWTRYNM |
| Mutation 7 | KFLYTAFAMQELGCNQNQ IFCKIPLELWTRYNM |
| Mutation 8 | KFLYTAFAMQELGCNQNQ AFCKIPLELWTRYNM |
| Mutation 9 | KFLYTAFAMQELGCNQNQ QFCKIPLELWTRYNM |
| Mutation 10 | KFLYTAFAMQELGCNQNQ RFCKIPLELWTRYNM |
| Region 727-762 | WNHGNITLGEWYNQTKDLQQKFYEIIMDIEQNNVQGKT |
| Mutation 1 | WNHGNITLGEWYNQTKDLQ NKFYEIIMDIEQNNVQGKT |
| Mutation 2 | WNHGNITLGEWYNQTKDLQ HKFYEIIMDIEQNNVQGKT |
| Mutation 3 | WNHGNITLGEWYNQTKDLQ SKFYEIIMDIEQNNVQGKT |
| Mutation 4 | WNHGNITLGEWYNQTKDLQ AKFYEIIMDIEQNNVQGKT |
| Mutation 5 | WNHGNITLGEWYNQTKDLQ GKFYEIIMDIEQNNVQGKT |
| Mutation 6 | WNHGNITLGEWYNQTKDLQ EKFYEIIMDIEQNNVQGKT |

The invention claimed is:
1. A polynucleotide encoding a polypeptide comprising a peptide sequence selected from the group consisting of SEQ ID NOs: 99 and 100.

* * * * *